(12) United States Patent
Kim et al.

(10) Patent No.: US 9,748,069 B2
(45) Date of Patent: Aug. 29, 2017

(54) X-RAY GENERATOR AND X-RAY IMAGING APPARATUS INCLUDING THE SAME

(71) Applicant: SAMSUNG ELECTRONICS CO., LTD., Suwon-si (KR)

(72) Inventors: Jong-pil Kim, Yongin-si (KR); Woo-sup Han, Yongin-si (KR); Kyung-hun Yoon, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 106 days.

(21) Appl. No.: 14/315,519

(22) Filed: Jun. 26, 2014

(65) Prior Publication Data

US 2015/0003585 A1 Jan. 1, 2015

(30) Foreign Application Priority Data

Jun. 26, 2013 (KR) .................... 10-2013-0073969

(51) Int. Cl.
*H01J 35/06* (2006.01)
*H01J 35/08* (2006.01)
*A61B 6/02* (2006.01)
*A61B 6/00* (2006.01)

(52) U.S. Cl.
CPC ............ *H01J 35/065* (2013.01); *A61B 6/02* (2013.01); *A61B 6/025* (2013.01); *A61B 6/4007* (2013.01); *A61B 6/502* (2013.01); *H01J 35/08* (2013.01); *H01J 2235/068* (2013.01); *H01J 2235/087* (2013.01); *H01J 2235/088* (2013.01)

(58) Field of Classification Search
CPC . H01J 35/08; H01J 2235/086; H01J 2235/084
See application file for complete search history.

(56) References Cited

U.S. PATENT DOCUMENTS

| 4,340,816 A | 7/1982 | Schott |
| 6,185,276 B1 | 2/2001 | Eastman |
| 6,480,565 B1 | 11/2002 | Ning |
| 7,123,689 B1 | 10/2006 | Wilson |
| 7,359,484 B2 | 4/2008 | Qiu et al. |
| 7,431,500 B2 | 10/2008 | Deych et al. |
| 7,496,176 B2 | 2/2009 | Aslund |
| 7,864,917 B2 | 1/2011 | Ribbing et al. |
| 7,978,816 B2 | 7/2011 | Matsuura et al. |

(Continued)

FOREIGN PATENT DOCUMENTS

| JP | H06124671 A | 5/1994 |
| JP | 2009193861 A | 8/2009 |

(Continued)

OTHER PUBLICATIONS

Communication dated Oct. 28, 2014, issued by the European Patent Office in counterpart European Application No. 14173681.9.

(Continued)

*Primary Examiner* — Hoon Song
(74) *Attorney, Agent, or Firm* — Sughrue Mion, PLLC

(57) ABSTRACT

An X-ray includes: electron emission devices that are arranged in one dimension or in two dimensions and are configured to emit electrons; and an anode electrode configured to emit an X-ray by using the electrons emitted by the electron emission devices and comprising regions having irregular thicknesses.

16 Claims, 22 Drawing Sheets

(56) References Cited

U.S. PATENT DOCUMENTS

| | | | |
|---|---|---|---|
| 7,991,120 B2 | 8/2011 | Okunuki et al. | |
| 2003/0198318 A1 | 10/2003 | Price et al. | |
| 2005/0117705 A1* | 6/2005 | Morrison | G21K 1/06 378/136 |
| 2007/0153979 A1* | 7/2007 | Baumann | G01N 23/04 378/138 |
| 2007/0165781 A1 | 7/2007 | Aslund | |
| 2011/0069808 A1 | 3/2011 | DeFreitas et al. | |
| 2011/0075809 A1 | 3/2011 | Boese et al. | |
| 2011/0255664 A1* | 10/2011 | Ueda | H01J 35/065 378/62 |
| 2012/0008739 A1 | 1/2012 | Hoernig et al. | |
| 2012/0201353 A1* | 8/2012 | Kim | G03B 42/02 378/62 |

FOREIGN PATENT DOCUMENTS

| | | |
|---|---|---|
| KR | 10-0933118 B1 | 12/2009 |
| KR | 10-2012-0108843 A | 10/2012 |
| WO | 2012005128 A1 | 1/2012 |

OTHER PUBLICATIONS

U.S. Appl. No. 14/316,091, Byoung-hoon Koh, filed Jun. 26, 2014.
U.S. Appl. No. 14/315,838, Jong-pil Kim, filed Jun. 26, 2014.
U.S. Appl. No. 14/315,733, Jong-pil Kim, filed Jun. 26, 2014.
U.S. Appl. No. 14/315,615, Byoung-hoon Koh, filed Jun. 26, 2014.
U.S. Appl. No. 14/316,016, Jong-pil Kim, filed Jun. 26, 2014.
U.S. Appl. No. 14/315,734, Jong-pil Kim, filed Jun. 26, 2014.

\* cited by examiner

X-RAY GENERATOR AND X-RAY IMAGING APPARATUS INCLUDING THE SAME

CROSS-REFERENCE TO RELATED APPLICATION

This application claims priority from Korean Patent Application No. 10-2013-0073969, filed on Jun. 26, 2013, in the Korean Intellectual Property Office, the disclosure of which is incorporated herein in its entirety by reference.

BACKGROUND

1. Field

One or more exemplary embodiments relate to an X-ray generator and an X-ray imaging apparatus including the X-ray generator.

2. Description of the Related Art

X-rays are used in non-destructive testing, structural and physical properties testing, image diagnosis, security inspection, and the like in the fields of industry, science, medical treatment, etc. An X-ray imaging system includes an X-ray generator for irradiating an X-ray and an X-ray detector for detecting X-rays that have passed through an object.

Recently, the X-ray detector is being rapidly converted from a film method to a digital method, whereas the X-ray generator uses an electron generation device using a tungsten filament type cathode. Thus, a single electron generation device is mounted in a single X-ray imaging apparatus. The X-ray detector is generally implemented as a flat panel detector, which is problematic in that there is a distance between the X-ray generator and the object to obtain an image from the single electron generation device. Furthermore, the object needs to be imaged from a single X-ray generator, which makes it difficult to select and image a specific part of the object.

SUMMARY

Exemplary embodiments may address at least the above problems and/or disadvantages and other disadvantages not described above. The exemplary embodiments are not required to overcome the disadvantages described above, and may not overcome any of the problems described above.

One or more exemplary embodiments include an X-ray imaging apparatus including a flat panel type X-ray generator and a method of operating the X-ray imaging apparatus.

One or more exemplary embodiments include an X-ray imaging apparatus capable of obtaining a tomography image and a method of operating the X-ray imaging apparatus.

One or more exemplary embodiments include an X-ray generator capable of adjusting a radiation angle of an X-ray, an X-ray imaging apparatus including the X-ray generator, and a method of operating the X-ray imaging apparatus.

One or more exemplary embodiments include an X-ray imaging apparatus for detecting an object and radiating an X-ray only to the object and a method of operating the X-ray imaging apparatus.

According to an aspect of an exemplary embodiment, an X-ray generator includes: a plurality of electron emission devices that are arranged in one dimension or in two dimensions and are for emitting electrons; and an anode electrode for emitting an X-ray by using the electrons emitted by the plurality of electron emission devices and including regions having an irregular thickness.

The anode electrode may be symmetrical to each other with respect to a center axis of the X-ray generator.

The thickness may increase the farther away from the center axis of the X-ray generator.

The thickness may decrease the farther away from the center axis of the X-ray generator.

At least one of surfaces of the anode electrode on which the electrons are incident and from which the X-ray is emitted may be a curved surface.

At least one of surfaces of the anode electrode on which the electrons are incident and from which the X-ray is emitted may be at least one of concave and convex surfaces.

At least one of surfaces of the anode electrode on which the electrons are incident or from which the X-ray is emitted may be a flat surface.

The anode electrode may include first and second layers formed of different materials.

The first and second layers may be disposed in parallel to the plurality of electron emission devices.

A wavelength of an X-ray emitted from the first layer and a wavelength of an X-ray emitted from the second layer may be different from each other.

When at least one of the electrons is incident on the first layer, the electrons may be not incident on the second layer.

At least one of the plurality of electron emission devices may include: a cathode electrode; a gate electrode spaced apart from the cathode electrode; and a plurality of electron emission sources that are disposed on the cathode electrode and are for emitting electrons due to a voltage difference between the cathode electrode and the gate electrode.

The cathode electrode included in each of the plurality of electron emission devices may be formed on the same substrate.

The gate electrode may include a mesh structure.

The X-ray generator may further include: a plurality of gate insulation layers disposed between the cathode electrode and the gate electrode.

The plurality of gate insulation layers and the plurality of electron emission sources may be alternately disposed.

According to an aspect of an exemplary embodiment, an X-ray generator includes: an electron emission device for emitting electrons; and an anode electrode for emitting X-rays by using the electrons emitted by the electron emission device and including regions having an irregular thickness.

The anode electrode may be symmetrical to each other with respect to a center axis of the X-ray generator.

At least one of surfaces of the anode electrode on which the electrons are incident and from which the X-rays are emitted may be at least one of concave and convex surfaces.

According to an aspect of an exemplary embodiment, an X-ray imaging apparatus includes: the X-ray generator; and an X-ray detector, with an object disposed between the X-ray generator and the X-ray detector, for detecting an X-ray that is transmitted to the object.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
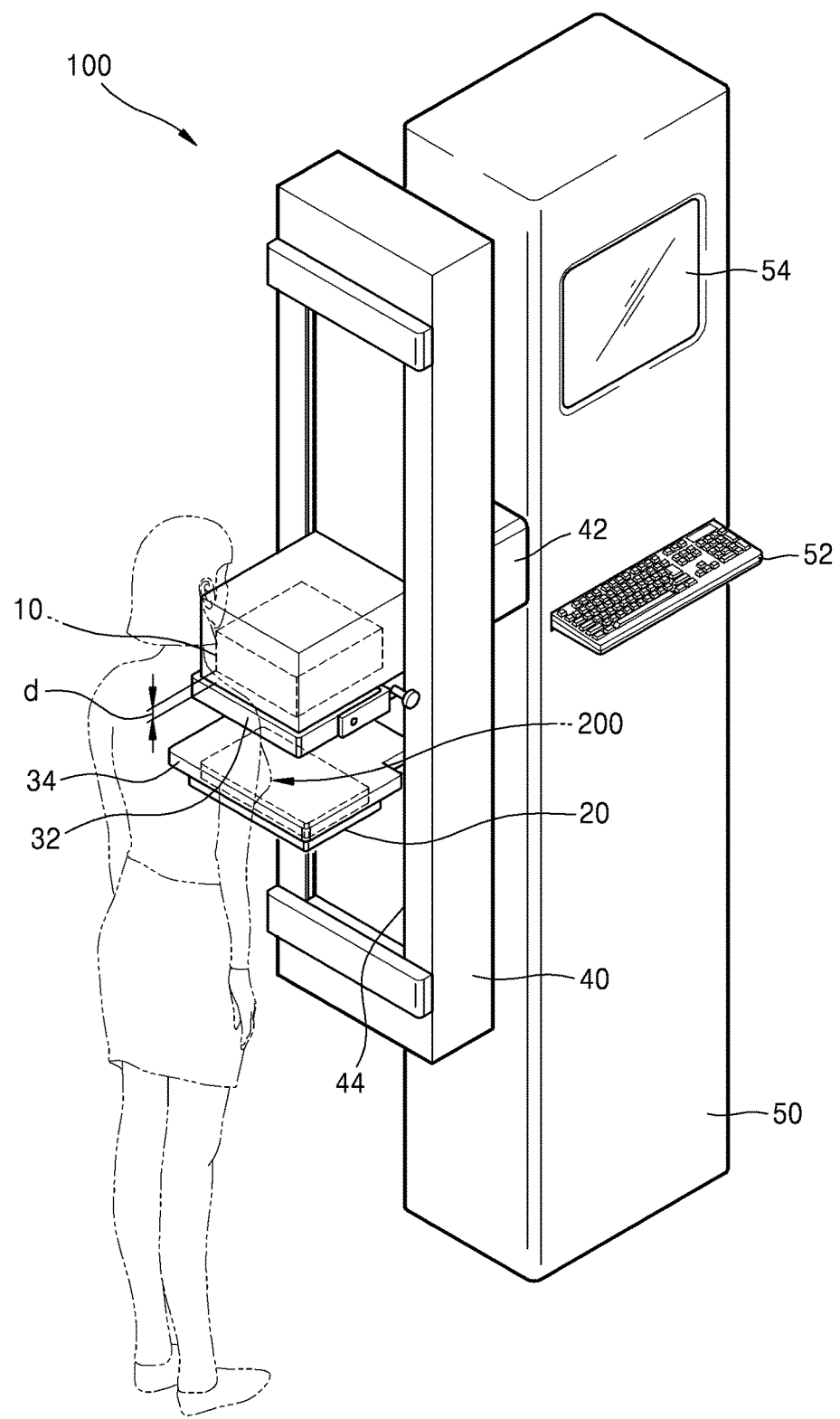
FIG. 1 is a schematic perspective view of an X-ray imaging apparatus according to an exemplary embodiment.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

In the present specification, an object may include a human being or an animal, or a part of the human being or the animal. For example, the object may include organs, such as the liver, the heart, the uterus, the brain, breasts, the abdomen, or blood vessels. In the present specification, a "user" is a medical expert, for example, a doctor, a nurse, a medical specialist, and a medical imaging expert, or an engineer managing medical apparatuses; however, an exemplary embodiment is not limited thereto.

Expressions such as "at least one of," when preceding a list of elements, modify the entire list of elements and do not modify the individual elements of the list.

FIG. 1 is a schematic perspective view of an X-ray imaging apparatus 100 according to an exemplary embodiment. The X-ray imaging apparatus 100 of FIG. 1 is a mammography apparatus that images a breast but is not limited thereto. The X-ray imaging apparatus 100 of an exemplary embodiment may apply to an X-ray imaging apparatus that contacts an object and generates an X-ray.

Referring to FIG. 1, the X-ray imaging apparatus 100 includes an X-ray generator 10 that generates the X-ray, an X-ray detector 20 that detects the X-ray that is transmitted to an object 200, and first and second panels 32 and 34 that may contact the object 200. The X-ray imaging apparatus 100 may further include a gantry 40 that supports the X-ray generator 10, the X-ray detector 20, and the panels 32 and 34, and a main body 50 that supports the gantry 40.

The main body 50 may include a user input device 52 that may input a user command to operate the X-ray imaging apparatus 100, a processor (not shown) that generates an image corresponding to the transmitted X-ray, a display 54 that displays the generated image, and a controller (not shown) that controls operations of the X-ray imaging apparatus 100. The user input device 52, the processor (not shown), the display 54, and the controller are not be necessarily included in the main body 50, and may be implemented as external devices that may communicate with the X-ray imaging apparatus 100 by wire or wirelessly.

The gantry 40 may be fixed to the main body 50 via a gantry driver 42. The gantry 40 may be disposed in one side surface of the main body 50 longitudinally. The gantry driver 42 may rotate the gantry 40 by 360° or at an angle. The gantry driver 42 may operate to move the gantry 40 up and down longitudinally with respect to the main body 50 so that a height of the gantry 40 may be adjusted in accordance with the object 200, and may rotate the gantry 42.

The panels 32 and 34 that may contact the object 200 and may be disposed on the front of the gantry 40. The first and second panels 32 and 34 may move up and down by using a guide groove 44 that is longitudinally included in the front of the gantry 40. Thus, if the object 200, for example, breasts of a patient, is placed between first and second panels 32 and 34, at least one of the first and second panels 32 and 34 may press the object 200 to compress the object 200. For example, the second panel 34 may be moved up or down to allow the object 200 to be placed on the second panel 34 and then the first panel 32 may be moved down to press the object 200 and compress the object 200.

The X-ray generator 10 that generates the X-ray may be disposed on the first panel 32. The X-ray generator 10 may be moved further away from or closer to the object 200 while maintaining a distance d with the first panel 32. For example, the X-ray generator 10 may be integrated with the first panel 32 so that the X-ray generator 10 and the first panel 32 may move along the guide groove 44.

In more detail, when the first panel 32 presses the object 200, since the X-ray generator 10 radiates the X-ray to the object 200, a distance between the X-ray generator 10 and the object 200 may be minimized. For example, the distance between the X-ray generator 10 and the object 200 may be about 10 cm. Thus, radiation of the X-ray to a region other than the object 200 may be prevented, thereby minimizing an X-ray radiation dose. To minimize the distance between the X-ray generator 10 and the object 200, the X-ray generator 10 may be disposed to contact a top side of the object 200. The X-ray generator 10 includes a plurality of X-ray generation units 300, which will be described later.

The X-ray detector 20 that detects the X-ray that is transmitted to the object 200 may be provided under the second panel 34. The X-ray detector 20 may be moved further away from or closer to the object 200 while maintaining a distance d with the second panel 34. For example, the X-ray detector 20 may be integrated with the second panel 34 so that the X-ray detector 20 and the second panel 34 may move along the guide groove 44.

In more detail, when the object 200 is placed on the second panel 34, since the X-ray detector 20 detects the X-ray that is transmitted to the object 200, a distance between the X-ray detector 20 and the object 200 may be minimized. Thus, the X-ray may be more exactly detected. To minimize the distance between the X-ray detector 20 and the object 200, the X-ray detector 20 may be disposed to contact a bottom side of the object 200. The X-ray detector 20 includes a plurality of X-ray detection units, which will be described later.

Figure 2A:
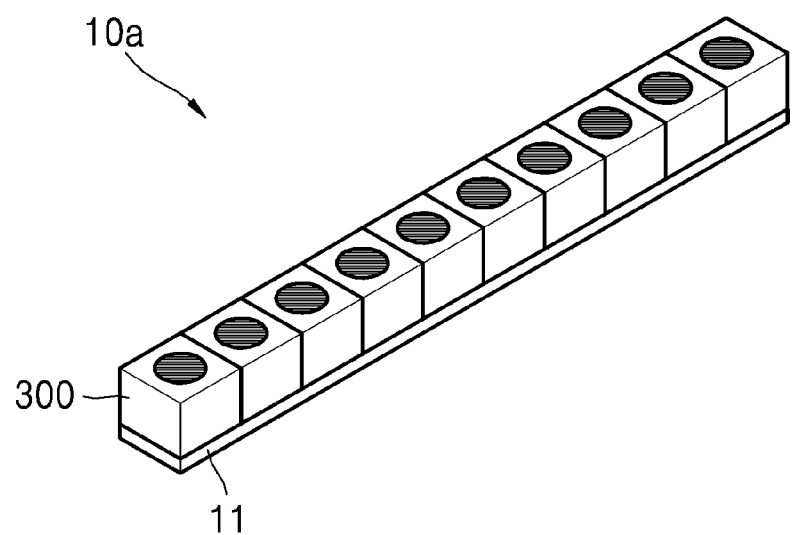
FIGS. 2A and 2B are schematic diagrams of X-ray generators according to an exemplary embodiment.
Figure 2B:
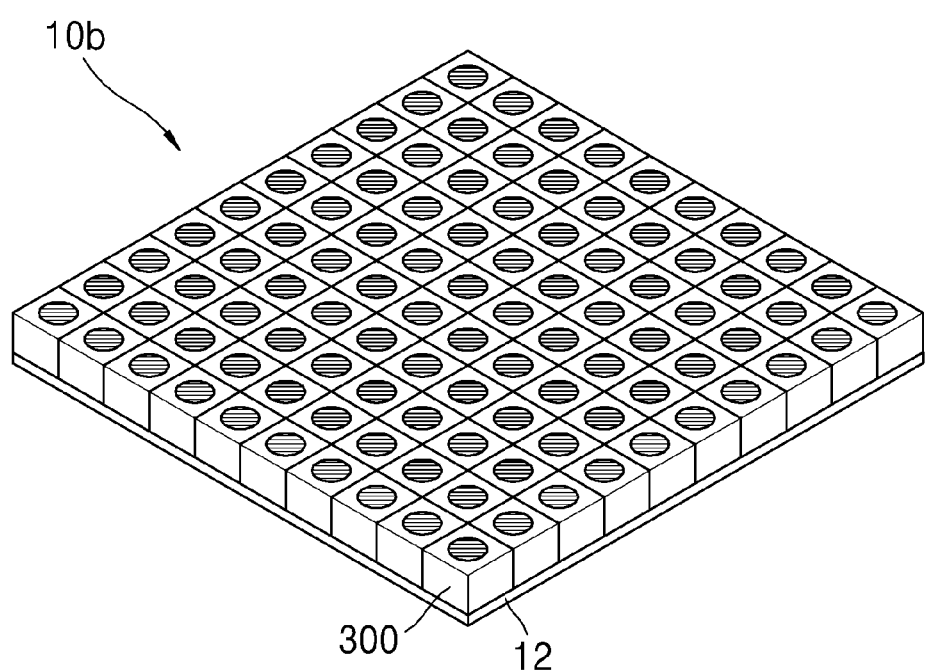

The X-ray generator 10 will now be described in more detail below. FIGS. 2A and 2B are schematic diagrams of X-ray generators 10a and 10b including the plurality of X-ray generation units 300 according to an exemplary embodiment. Referring to FIG. 2A, the X-ray generator 10a may include the X-ray generation units 300 arranged in one dimension, i.e., as a 1D array. Referring to FIG. 2B, the X-ray generator 10b may include the X-ray generation units 300 arranged in two dimensions, i.e., as a 2D array.

Each of the X-ray generation units 300 may be independently driven to generate an X-ray. Accordingly, all of the X-ray generation units 300 may be driven to radiate X-rays to the object 200 or some of the X-ray generation units 300 are driven to radiate X-rays to the object 200. At least one of the X-ray generation units 300 may radiate X-rays to all regions of the object 200 or a specific region. In addition, at least one of the X-ray generation units 300 may be simultaneously or sequentially driven with one or more other ones of the X-ray generation units 300. For example, only some X-ray detection units corresponding to the X-ray generation units 300 that are being driven may be driven.

Although the X-ray generation units 300 are respectively formed on a single substrate 11 and 12 in FIGS. 2A and 2B, an exemplary embodiment is not limited thereto. Each of the X-ray generation units 300 may be separately manufactured and the X-ray generation units 300 may be assembled into the X-ray generators 10a and 10b. Alternatively, some of the X-ray generation units 300 may be formed on a single substrate and then assembled together with other X-ray generation units 300 formed on other substrates. For example, a 2D X-ray generator may be manufactured by generating X-ray generators in one dimension on a single substrate and arranging the substrates with X-ray generators in another. Although not shown, an X-ray controller for controlling a proceeding path of an X-ray generated by each of the X-ray generation units 300 to not interfere with a neighboring X-ray may be provided. In the X-ray control unit, an opening is formed in an area corresponding to each of the X-ray generation units 300 and an X-ray absorbing material may be formed in a grid type in the other area (for example, a boundary area between the neighboring X-ray generation units 300).

Figure 3A:
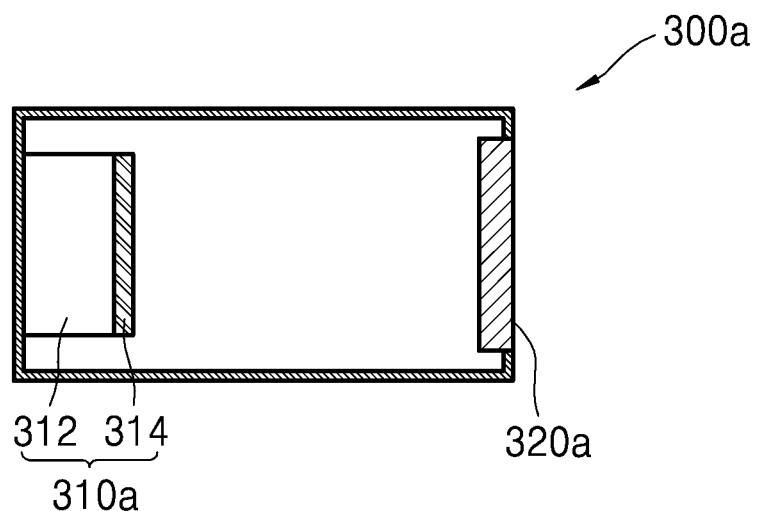
FIGS. 3A, 3B, 3C, and 3D are schematic diagrams of X-ray generation units according to an exemplary embodiment.

FIGS. 3A to 3D are schematic diagrams of X-ray generation units 300a, 300b, 300c, and 300d according to an exemplary embodiment. Referring to FIG. 3A, the X-ray generation unit 300a may include an electron emission device 310a that may emit electrons and an anode electrode 320a that may emit an X-ray by collision of the emitted electrons. The anode electrode 320a may include metal or a metal alloy such as W, Mo, Ag, Cr, Fe, Co, Cu, etc.

The electron emission device 310a may include a cathode electrode 312 and an electron emission source 314 which is arranged on the cathode electrode 312 and emits electrons. The cathode electrode 312 may be metal such as Ti, Pt, Ru, Au, Ag, Mo, Al, W, or Cu, or a metal oxide such as indium tin oxide (ITO), aluminum zinc oxide (AZO), indium zinc oxide (IZO), tin oxide ($SnO_2$), or indium oxide ($In_2O_3$). The electron emission source 314 may be formed of a material capable of emitting electrons. For example, the electron emission source 314 may be formed of metal, silicon, an oxide, diamond, diamond like carbon (DLC), a carbide compound, a nitrogen compound, carbon nanotube, carbon nanofiber, etc.

The cathode electrode 312 applies a voltage to the electron emission source 314. When a voltage difference occurs between the electron emission source 314 and the anode electrode 320a, that is, the cathode electrode 312 and the anode electrode 320a, the electron emission source 314 emits electrons and the electrons collide with the anode electrode 320a. Accordingly, the anode electrode 320a radiates an X-ray due to the collision of electrodes.

Figure 3B:
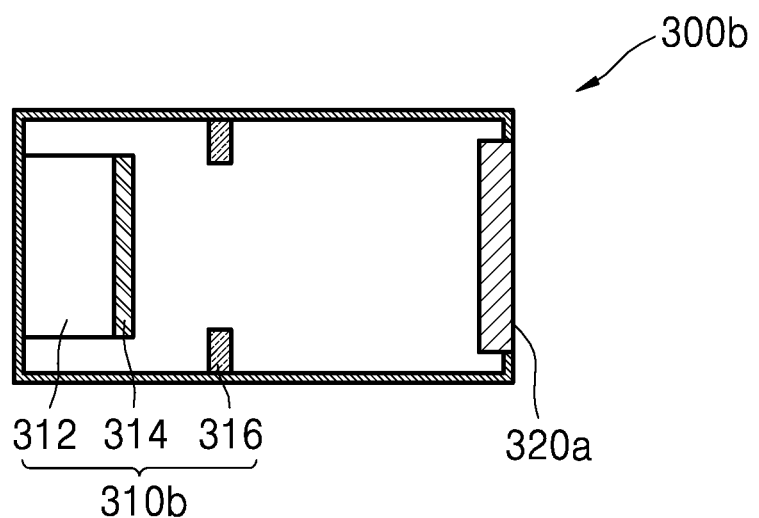

As shown in FIG. 3B, an electron emission device 310b of the X-ray generation unit 300b may further include a gate electrode 316 between the electron emission source 314 and the anode electrode 320a. The gate electrode 316 may be formed of the same material as the cathode electrode 312. The electron emission source 314 may emit electrons by the voltage difference between the gate electrode 316 and the cathode electrode 312. As the gate electrode 316 is arranged between the cathode electrode 312 and the anode electrode 320a, the electrons induced by the electron emission source 314 by the voltage applied to the gate electrode 316 may be controlled. Accordingly, the X-ray generation unit 300b may more stably control the emission of electrons.

Figure 3C:
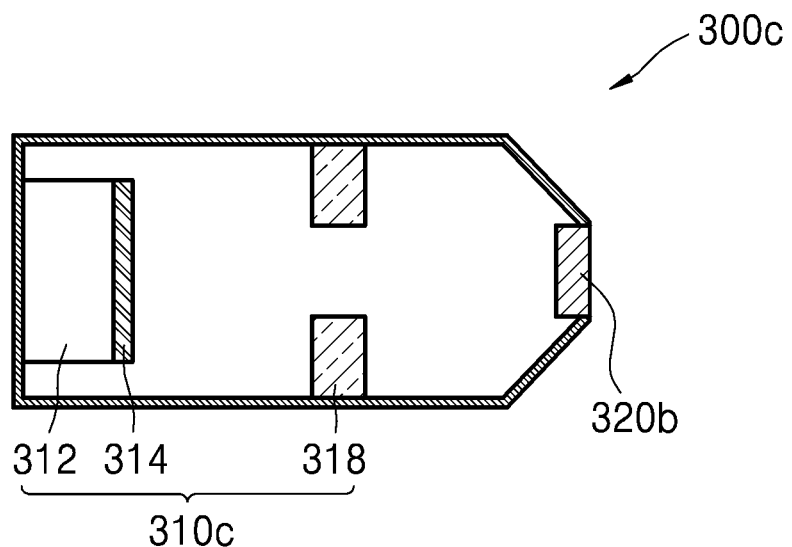

As shown in FIG. 3C, an electron emission device 310c of the X-ray generation unit 300c may include a focusing electrode 318 between the electron emission source 314 and an anode electrode 320b. The focusing electrode 318 may be formed of the same material as the cathode electrode 312. The focusing electrode 318 focuses the electrons emitted from the electron emission source 314 on an area of the anode electrode 320b to collide therewith. A voltage applied to the focusing electrode 318 may be the same as or similar to the voltage applied to the gate electrode 316 so that an optimal focusing performance may be maintained.

Figure 3D:
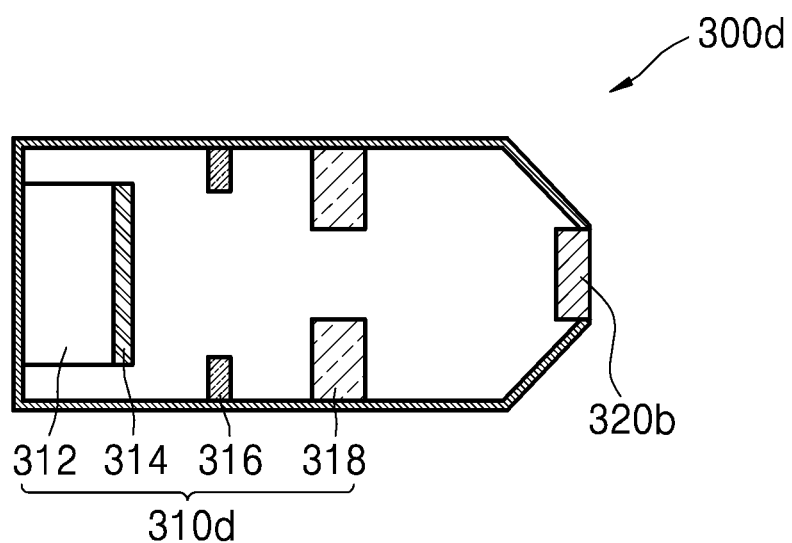

As shown in FIG. 3D, an electron emission device 310d of the X-ray generation unit 300d may include the cathode electrode 312, the electron emission source 314 that is arranged on the cathode electrode 312 and emits electrons, the gate electrode 316 spaced apart from the cathode electrode 312, and the focusing electrode 318 focusing the emitted electrons.

Figure 4:
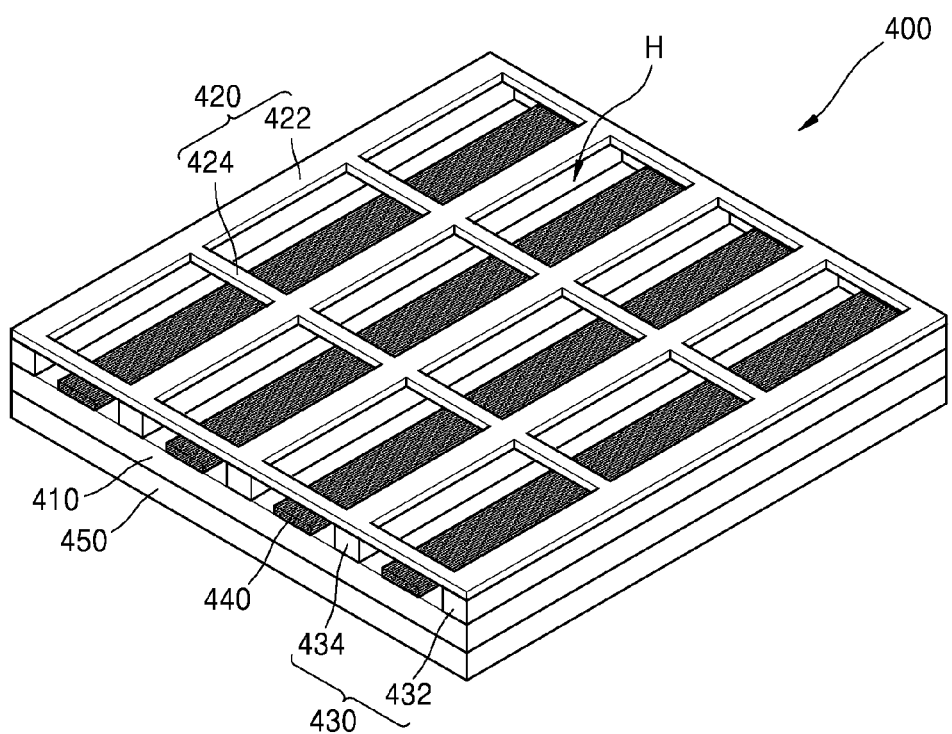
FIG. 4 illustrates an electron emission device, according to an exemplary embodiment.

FIG. 4 illustrates an electron emission device 400 including a gate electrode 420, according to an exemplary embodiment.

Referring to FIG. 4, the electron emission device 400 may include a cathode electrode 410, the gate electrode 420 having a mesh structure spaced apart from the cathode electrode 410, a plurality of insulation layers 430 and a plurality of electron emission sources 440 that extend in a first direction between the cathode electrode 410 and the gate electrode 420 and are spaced apart from each other. A substrate 450 for supporting the electron emission device 400 may be formed of an insulation material such as glass.

The substrate 450 may support a single electron emission device 400 or a plurality of the electron emission devices.

The cathode electrode 410 and the gate electrode 420 may be formed of a conductive material. The cathode electrode 410 may apply a voltage to each of the electron emission sources 440 and may have a flat panel shape. When the cathode electrode 410 has a flat panel shape, the substrate 450 may be omitted. The gate electrode 420 may have a mesh structure including a plurality of openings H. For example, the gate electrode 420 may include a plurality of gate lines 422 separated from each other and arranged on the insulation layers 430 and a plurality of gate bridges 424 connecting the gate lines 422. Accordingly, the two neighboring gate lines 422 and the two neighboring gate bridges 424 form one opening H.

The openings H may be arranged to expose at least a part of the electron emission sources 440 between the insulation layers 430. Since the gate electrode 420 has a mesh structure, a large electron emission device 400 may be manufactured. Although the openings H of the gate electrode 420 are each rectangular in FIG. 4, an exemplary embodiment is not limited thereto. Shapes of the openings H may be at least one of circles, ovals, and polygons. The sizes of the openings H may be identical or different.

The insulation layers 430 are arranged between the cathode electrode 410 and the gate electrode 420 and prevent electrical connection between the cathode electrode 410 and the gate electrode 420. The insulation layers 430 are arranged in multiple numbers and at least three insulation layers 430 may be provided. The insulation layers 430 may have a linear shape. The insulation layers 430 extend in one direction and are separate from one another in another direction and support the gate electrode 420. The insulation layers 430 may each include a first insulation layer 432 supporting an edge area of the gate electrode 420 and a second insulation layer 434 supporting a middle area of the gate electrode 420.

The insulation layers 430 may be formed of an insulation material used for a semiconductor device. For example, the insulation layers 430 may be formed of at least one high-K material, as for example, hafnium oxide ($HfO_2$), aluminum oxide ($Al_2O_3$), and/or silicon nitride ($Si_3N_4$), which are high-K materials having a higher dielectric rate than, for example, silicon dioxide ($SiO_2$).

Although the insulation layers 430 have a linear shape in FIG. 4, an exemplary embodiment is not limited thereto. For example, the second insulation layer 434 may have a column shape and may be arranged under the gate lines 422.

The electron emission sources 440 emit electrons due to the voltage applied to the cathode electrode 410 and the gate electrode 420. The electron emission sources 440 may be alternately arranged between the insulation layers 430. For example, the electron emission sources 440 may be spaced apart from one another with the second insulation layer 434 interposed between the neighboring electron emission sources 440. The electron emission sources 440 may have a shape of strips extending in the first direction, like the second insulation layer 434.

The gate electrode 420 is arranged above the electron emission sources 440 which may be spaced apart from the gate electrode 420 to prevent the electron emission sources 440 and the gate electrode 420 from being short-circuited.

The electron emission sources 440 may be formed of a material capable of emitting electrons. As an area occupied by the electron emission sources 440 in the electron emission device 400 increases, the electron emission device 400 may emit a large amount of electrons. However, the electron emission device 400 may endure an electrostatic force due to a difference in the voltages applied between the electron emission sources 440 and the gate electrode 420. To prevent this problem, the insulation layers 430 and the electron emission sources 440 of an exemplary embodiment are alternately arranged, and the gate electrode 420 having the opening H is arranged over an area where each of the electron emission sources 440 is arranged, thereby implementing the large area electron emission device 400.

Since the gate electrode 420 includes the gate bridges 424 arranged in a direction crossing the lengthwise direction of the electron emission sources 440, a uniform electric field may be formed on surfaces of the electron emission sources 440.

Although the electron emission sources 440 are formed in strips in FIG. 4, an exemplary embodiment is not limited thereto. The electron emission sources 440 may be formed as a point type in an area corresponding to the opening H above the cathode electrode 410. The point-type electron emission sources 440 may be arranged in a 2D array, that is, in a matrix format.

Although the electron emission sources 440 are arranged in the single electron emission device 400 in FIG. 4, an exemplary embodiment is not limited thereto. Also, only one electron emission source may be arranged in the electron emission device 400 or two or more electron emission sources may be arranged therein.

A proceeding path of the X-ray may be controlled by the shape of an anode electrode. In detail, as the thickness of the anode electrode is provided to be irregular, the proceeding path of the X-ray radiated from the anode electrode may be controlled.

FIGS. 5A to 5G illustrate anode electrodes having irregular thicknesses according to an exemplary embodiment. The anode electrode illustrated in each of FIGS. 5A to 5G corresponds to a single X-ray generator. However, an exemplary embodiment is not limited thereto. One anode electrode may correspond to one electron emission device. For convenience of explanation, one anode electrode corresponding to the single X-ray generator will be described below.

As shown in FIGS. 5A to 5G, the anode electrode may be symmetrically provided about a center axis X of the X-ray generator 10 so that X-rays may be symmetrically radiated.

The thicknesses of anode electrodes 510 and 520 gradually decrease from the center axis X of the X-ray generator 10 toward edges thereof, and the X-rays radiated from the anode electrodes 510 and 520 may propagate to be focused at the center axis X of the X-ray generator 10. Thus, the X-ray generator 10 may efficiently radiate an X-ray in a partial area of the object.

In more detail, surfaces 512 and 522 of the anode electrodes 510 and 520, on which electrons are incident, may be flat surfaces, whereas surfaces 514 and 524 from which X-rays are emitted may be convex surfaces, with respect to the opposing surfaces 512 and 522. The surfaces 514 and 524 from which X-rays are emitted may be convexly curved surfaces or convex surfaces obtained by combining flat surfaces. A position where the X-ray is focused may be determined by an angle θ1 and a radius $R_1$ of the corresponding convex structures. Although in FIGS. 5A and 5B the surfaces 512 and 522 of the anode electrodes 510 and 520 on which electrons are incident are flat and the surfaces 514 and 524 from which X-rays are emitted are convex, an exemplary embodiment is not limited thereto. That is, the surfaces on which electrons are incident may be convex, whereas the surfaces from which X-rays are emitted may be flat.

Figure 5A:
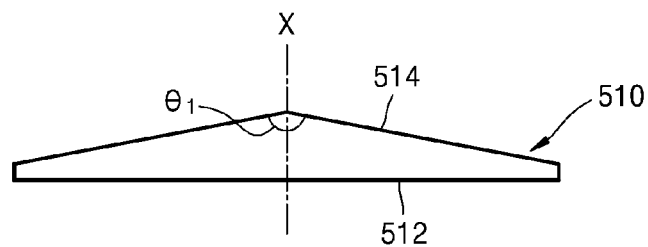
FIGS. 5A, 5B, 5C, 5D, 5E, 5F, and 5G illustrate anode electrodes having irregular thicknesses, according to an exemplary embodiment.
Figure 5B:
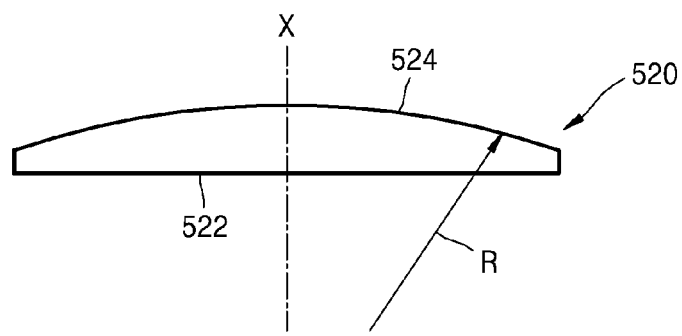
Figure 5C:
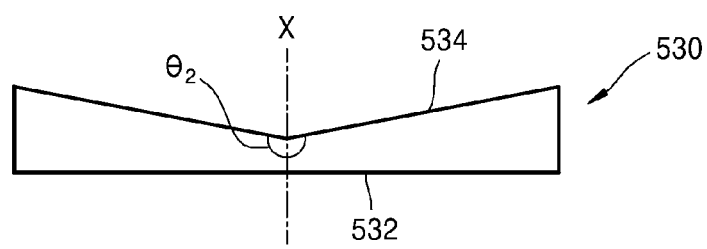
Figure 5D:
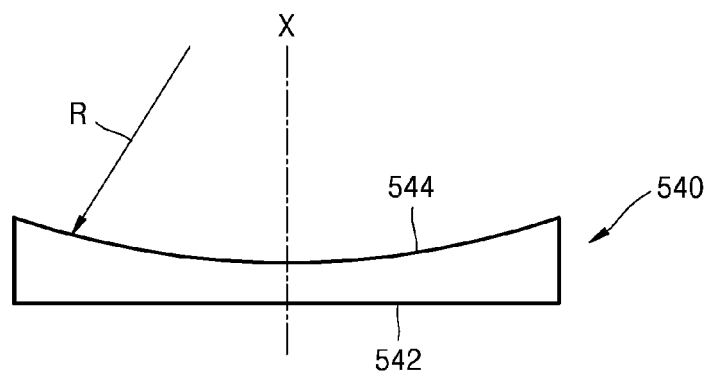

As illustrated in FIGS. 5C and 5D, the thicknesses of anode electrodes 530 and 540 gradually increase from the center axis X of the X-ray generator 10 toward edges thereof, and the X-ray radiated from each of the anode electrodes 530 and 540 may propagate toward an area larger than a sectional area of each of the anode electrodes 530 and 540. Thus, the X-ray generator 10 may radiate an X-ray to a relatively large area of an object.

In more detail, surfaces 532 and 542 of the anode electrode 530 and 540, on which electrons are incident, may be flat surfaces, whereas surfaces 534 and 544 from which X-rays are emitted may be concave surfaces, with respect to the opposing surfaces 532 and 542. The surfaces 534 and 544 from which X-rays are emitted may be concavely curved surfaces or concave surfaces obtained by combining flat surfaces. A size of an area where the X-ray is radiated may be determined by an angle θ2 and a radius R, of the corresponding concave structures. Although in FIGS. 5C and 5D the surfaces 532 and 542 of the anode electrodes 530 and 540 on which electrons are incident are flat and the surfaces 534 and 544 from which X-rays are emitted are concave, an exemplary embodiment is not limited thereto. That is, the surfaces on which electrons are incident may be concave, whereas the surfaces from which X-rays are emitted may be flat.

Figure 5E:
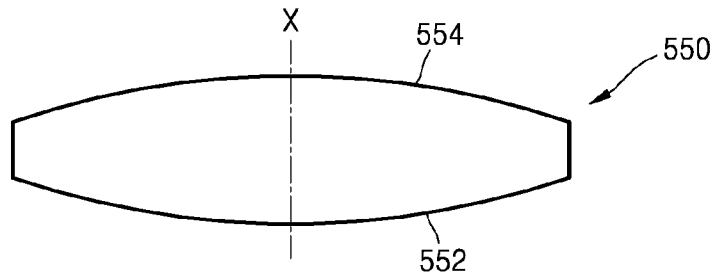

As shown in FIG. 5E, both surfaces 552 and 554 of an anode electrode 550 on which electrons are incident and from which X-rays are emitted may be convex. For example, a focal distance of an X-ray may become shorter. Alternatively, both surfaces on which electrons are incident and from which X-rays are emitted may be concave, with respect to one another. Alternatively, while one of the surfaces on which electrons are incident and from which X-rays are emitted may be concave, the other surface may be convex, with respect to one another.

Figure 5F:
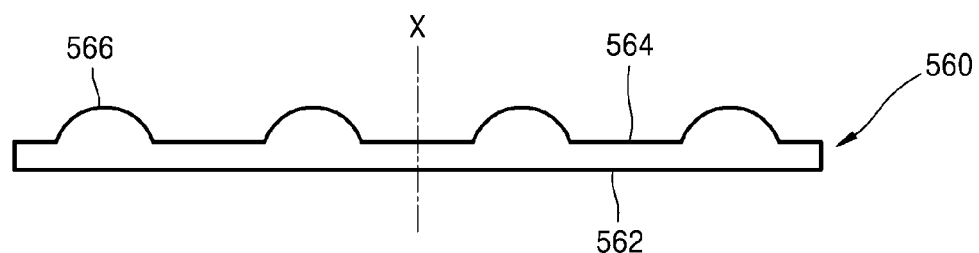
Figure 5G:
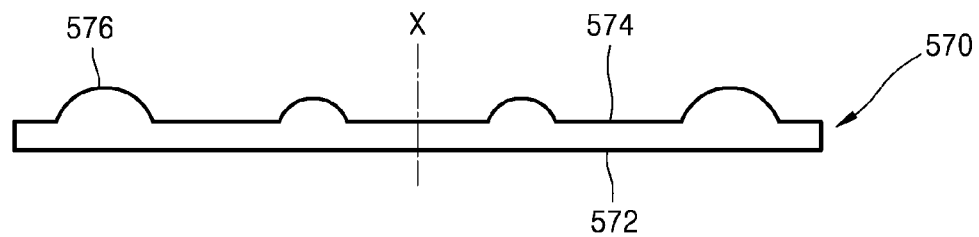

The thickness of an anode electrode may be partially irregular. For example, as illustrated in FIGS. 5F and 5G, anode electrodes 560 and 570 may have a shape in which only some portions are convex with respect to a bottom surface 562, 572, while other portions 564, 574 which are disposed between the convex portions 566, 576, have smaller thicknesses. A convex structure 566 may be identical to other convex structures or a convex structure 576 may be different from other convex structure according to an area. The thicknesses of the convex structures 576 may be symmetrical with respect to the center axis X of the X-ray generator 10. Although FIGS. 5F and 5G illustrate only a convex shape, an exemplary embodiment is not limited thereto. The anode electrode may have concave structures or both a concave structure and a convex structure, with respect to a bottom surface 562, 572.

As such, since the propagating path of an X-ray may be controlled by using the anode electrode having an irregular thickness, the X-ray generator 10 may efficiently radiate an X-ray to the object and may also reduce an unnecessary X-ray radiation dose.

Figure 6:
FIG. 6 illustrates an anode electrode having a uniform thickness, according to an exemplary embodiment.

The X-ray imaging apparatus 100 according to an exemplary embodiment may use an anode electrode having a uniform thickness. FIG. 6 illustrates an anode electrode 580 having a uniform thickness, according to an exemplary embodiment. Referring to FIG. 6, while the anode electrode 580 having a uniform thickness is used, the propagating path of an X-ray may be controlled by using a separate element such as a collimator (not shown).

Figure 7A:
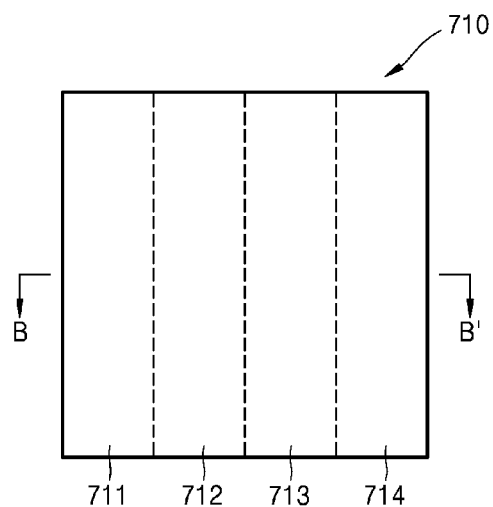
FIGS. 7A and 7B illustrate an anode electrode formed of different materials, according to an exemplary embodiment.
Figure 7B:
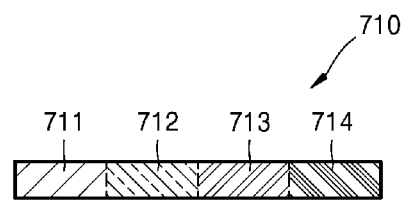

The anode electrode may include a plurality of layers formed of different materials and capable of radiating X-rays of different wavelengths. FIGS. 7A and 7B illustrate an anode electrode 710 formed of different materials, according to an exemplary embodiment. As shown in FIGS. 7A and 7B, the anode electrode 710 may include a plurality of layers 711, 712, 713, and 714 formed of different materials. The layers 711, 712, 713, and 714 may be parallelly arranged with respect to an electron emission device. The anode electrode 710 may radiate X-rays of different wavelengths according to the layers 711, 712, 713, and 714 with which electrons collide.

As another example, an anode electrode irradiating X-rays of multiple wavelengths may have a non-uniform thickness. FIGS. 8A, 8B, 8C, and 8D illustrate anode electrodes 810 and 820 formed of different materials, according to an exemplary embodiment. Each of the anode electrodes 810 and 820 may include a plurality of layers formed of different materials and at least one of the layers may have an irregular thickness.

Figure 8A:
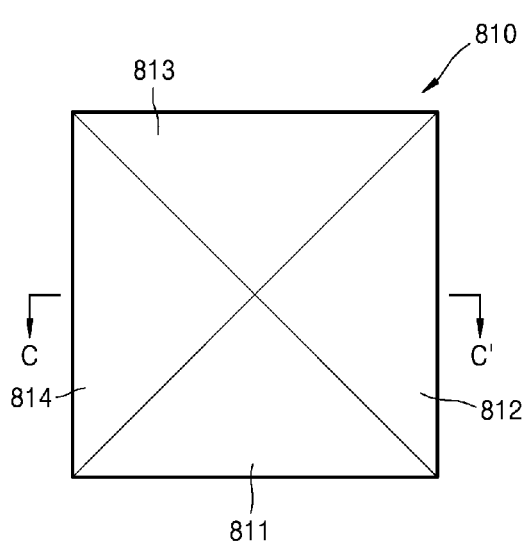
FIGS. 8A, 8B, 8C, and 8D illustrate anode electrodes formed of different materials, according to an exemplary embodiment.
Figure 8B:
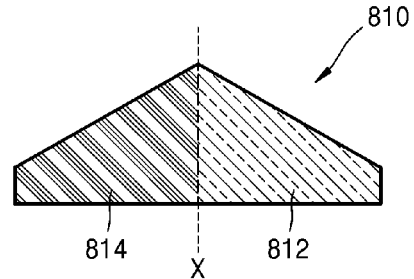

For example, as shown in FIGS. 8A and 8B, the anode electrode 810 may include a plurality of layers 811, 812, 813, and 814 that are formed of different materials. The layers 811, 812, 813, and 814 have thicknesses that gradually decrease from the center axis X of the X-ray generator 10 toward edges thereof. Accordingly, the anode electrode 810 may focus the radiated X-rays. Since the X-rays having different wavelengths are focused on different areas, a single linear X-ray generator may image many different areas at different depths of the object at one time.

Figure 8C:
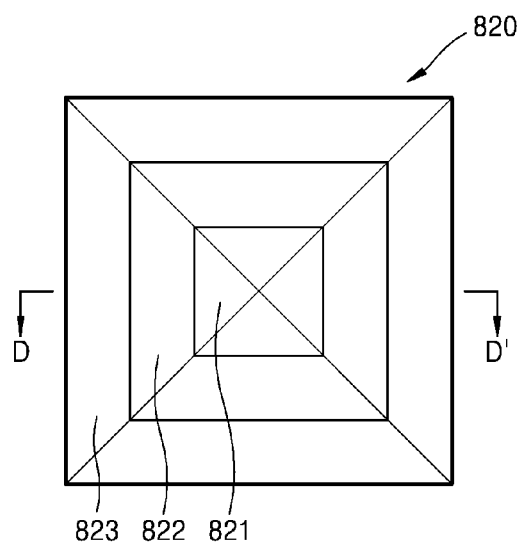
Figure 8D:
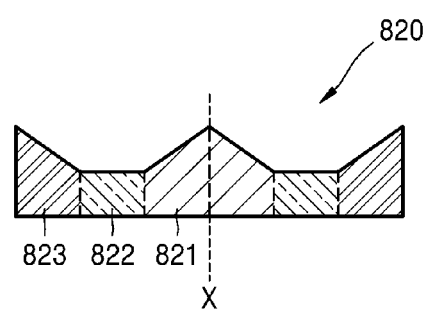

As shown in FIGS. 8C and 8D, the anode electrode 820 may include a plurality of layers 821, 822, and 823 that are formed of different materials. The anode electrode 820 may have a change in the thickness thereof according to the layers 821, 822, and 823. For example, the first layer 821 may have a thickness that gradually decreases from the center axis X of the X-ray generator 10 toward an edge thereof, the second layer 822 may have a uniform thickness, and the third layer 823 may have a thickness that gradually increases with respect to the center axis X of the X-ray generator 10 toward the edge thereof. Accordingly, the anode electrode 820 may radiate an X-ray to a larger surrounding area while focusing on an area of interest of the object.

Figure 9A:
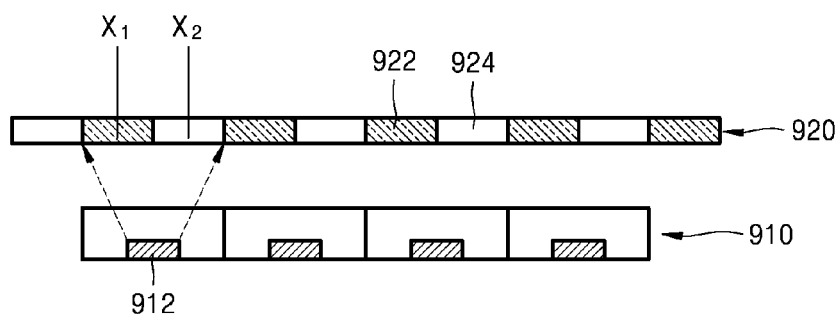
FIGS. 9A, 9B, and 9C illustrate an X-ray generator generating an X-ray of a short wavelength or an X-ray of a plurality of wavelength bands according to an exemplary embodiment.
Figure 9B:
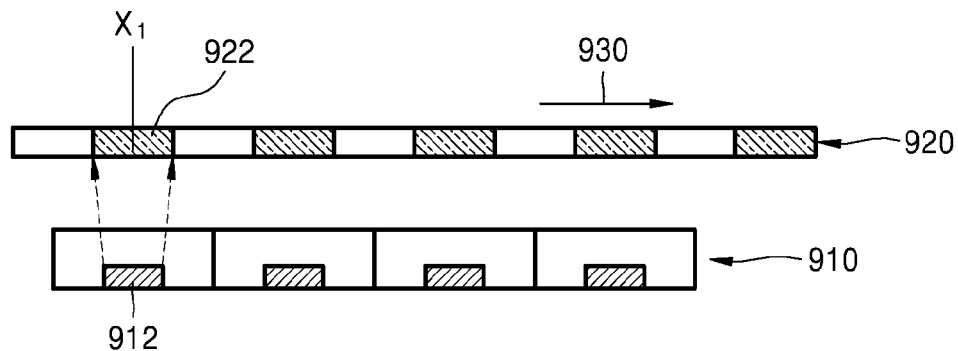
Figure 9C:
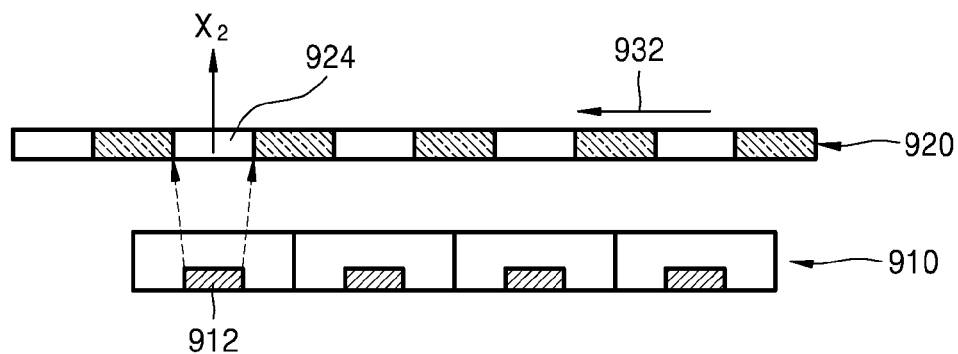

The X-ray generator 10 according to the present embodiment may simultaneously or selectively generate X-rays of different wavelengths. FIGS. 9A to 9C illustrate an X-ray generator generating an X-ray of a short wavelength or simultaneously generating X-rays of a plurality of wavelength bands, according to an exemplary embodiment.

Referring to FIG. 9A, a plurality of electron emission devices 910, each having an electron emission source 912, and an anode electrode 920 may be arranged separately from one another. In the anode electrode 920, first and second layers 922 and 924 that are formed of different materials may be alternately arranged. When the first and second layers 922 and 924 are disposed to overlap with each other in an area corresponding to the electron emission source 912 of one of the electron emission devices 910, electrons emitted by the electron emission devices 910 may collide with the first and second layers 922 and 924. Accordingly, the anode electrode 920 may simultaneously radiate a first X-ray X1 and a second X-ray X2 of different wavelengths.

In FIGS. 9B and 9C, the anode electrode 920 makes a translational movement in parallel with the electron emission devices 910 in one of a direction 930 and a direction 932. In FIG. 9B, the anode electrode 920 makes a translational movement in parallel with the electron emission devices 910 such that the first layer 922 of the anode electrode 920 may be arranged to overlap with the electron emission source 912. Then, the electrons emitted by the electron emission devices 910 collide with the first layer 922 and thus the first X-ray X1 of a first wavelength may be radiated from the anode electrode 920.

In FIG. 9C, the anode electrode 920 makes a translational movement in parallel with the electron emission devices 910 such that the second layer 924 of the anode electrode 920 may be arranged to overlap with the electron emission source 912. Then, the electrons emitted by the electron emission devices 910 collide with the second layer 924 and thus the second X-ray X2 of a second wavelength may be radiated from the anode electrode 920.

As such, since the anode electrode 920 simultaneously radiates a plurality of X-rays or selectively radiates a single X-ray, usability of the X-ray generator 10 may be improved.

As described above, X-ray generation units are arranged in an X-ray generator 10. Each of the X-ray generation units is separately manufactured as one unit and then the X-ray generation units are assembled, thereby forming the X-ray generator. A plurality of electron emission devices and an anode electrode may be integrally manufactured on a single substrate. Alternatively, a plurality of electron emission devices are manufactured on a single substrate and then an anode electrode is assembled, thereby forming a linear X-ray generator. The linear X-ray generator may be formed by a variety of methods.

The X-ray generator may further include a collimator (not shown) for controlling a proceeding direction of an X-ray. Accordingly, an unnecessary X-ray radiation dose may be reduced, and an X-ray may be more accurately detected.

Figure 10A:
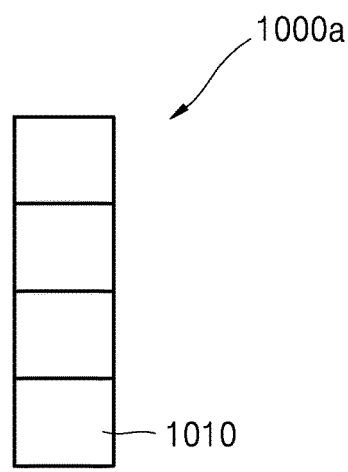
FIGS. 10A and 10B schematically illustrate X-ray detectors that may be applied to an X-ray detector of FIG. 1.
Figure 10B:
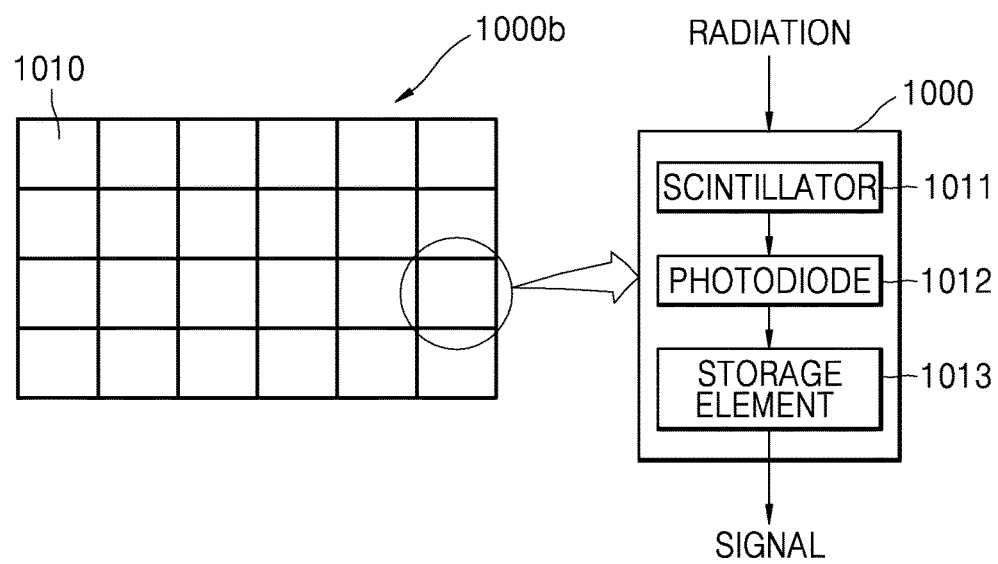

FIGS. 10A and 10B schematically illustrate X-ray detectors 1000a and 1000b that may be used as the X-ray detector 20 of FIG. 1. As shown in FIG. 10A, the X-ray detector 1000a may be configured as a plurality of X-ray detection units 1010 arranged in one dimension. Alternatively, as shown in FIG. 10B, the X-ray detector 1000b may be configured as the plurality of X-ray detection units 1010 arranged in two dimensions.

Each of the X-ray detection units 1010 is a light-receiving element that receives an X-ray and converts a received X-ray into an electric signal, and may include, for example, a scintillator 1011, a photodiode 1012, and a storage element 1013. The scintillator 1011 receives an X-ray and outputs photons, in particular visible photons, that is, a visible ray, according to a received X-ray. The photodiode 1012 receives the photons output from the scintillator 1011 and converts received photons into electric signals. The storage element 1013 is electrically connected to the photodiode 1012 and stores the electric signal output from the photodiode 1012. In this regard, the storage element 1013 may be, for example, a storage capacitor. The electric signal stored in the storage element 1013 of each of the X-ray detection units 1010 is applied to a processor (not shown) where the signal is processed into an X-ray image.

The X-ray detectors 1000a and 1000b may detect an X-ray by using a photoconductor directly converting an X-ray into an electric signal.

The X-ray detection units 1010 may be provided to correspond to the X-ray generation units 300 of an X-ray generator. The X-ray generation units 300 and the X-ray detection units 1010 may have a one-to-one correspondence. Each of the X-ray generation units 300 may correspond to two or more X-ray detection units 1010, or two or more X-ray generation units 300 may correspond to one X-ray detection unit 1010.

The X-ray detection units 1010 may be simultaneously or independently driven to detect an X-ray. Accordingly, an X-ray passing through the entire area of the object may be detected as all of the X-ray detection units 1010 are driven, or an X-ray passing through a particular area of the object may be detected as some of the X-ray detection units 1010 are driven. Also, at least one of the X-ray detection units 1010 may be simultaneously or sequentially driven.

Although the X-ray detection units 1010 are formed on a single substrate, an exemplary embodiment is not limited thereto. Each of the X-ray detection units 1010 is separately manufactured, and the X-ray detection units 1010 are assembled into the X-ray detectors 1000a and 1000b. Alternatively, some of the X-ray detection units 1010 are formed on a single substrate and then assembled together with the other X-ray detection units 1010 formed on other substrates. For example, X-ray detectors in one dimension are generated on a single substrate and then are arranged, and thus X-ray detectors in two dimensions may be manufactured.

When an X-ray generation area of the X-ray generator and X-ray detection areas of the X-ray detectors 1000a and 1000b are equal to or larger than a test area of the object, the linear X-ray generator and the X-ray detectors 1000a and 1000b may image the object by performing one operation. The X-ray imaging apparatus 100 may image the whole object at one time or a partial area of the object. When a partial area of the object is to be imaged, only some of the X-ray generation units 300 of the X-ray generator may operate to generate an X-ray, and only some of the X-ray detection units 1010 corresponding to the operating X-ray generation units 300 may be synchronized to detect the X-ray.

However, when at least one of the X-ray generation area of the X-ray generator and the X-ray detection areas of the X-ray detectors 1000a and 1000b is smaller than the test area of the object, at least one of the X-ray generator and the X-ray detectors 1000a and 1000b may move to be driven two times or more.

Figure 11A:
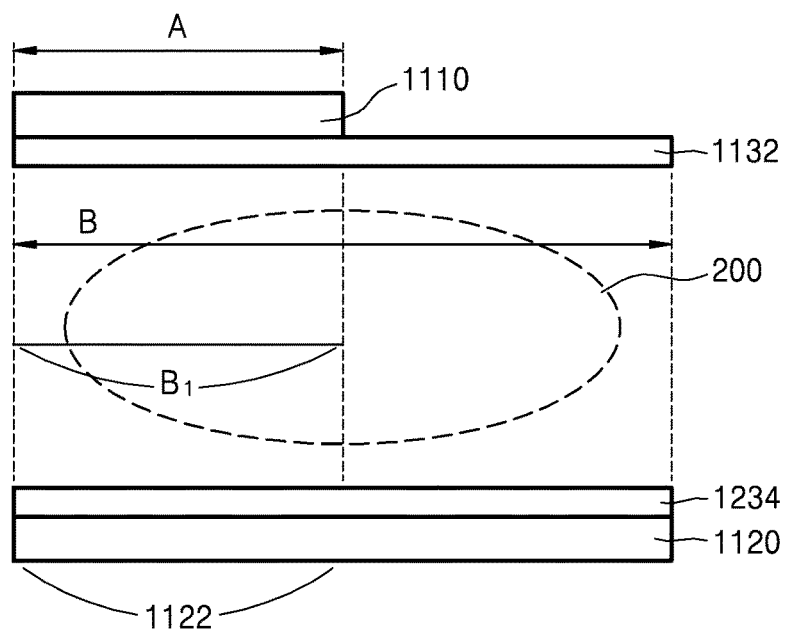
FIGS. 11A and 11B are diagrams for describing an X-ray imaging method according to an exemplary embodiment.
Figure 11B:
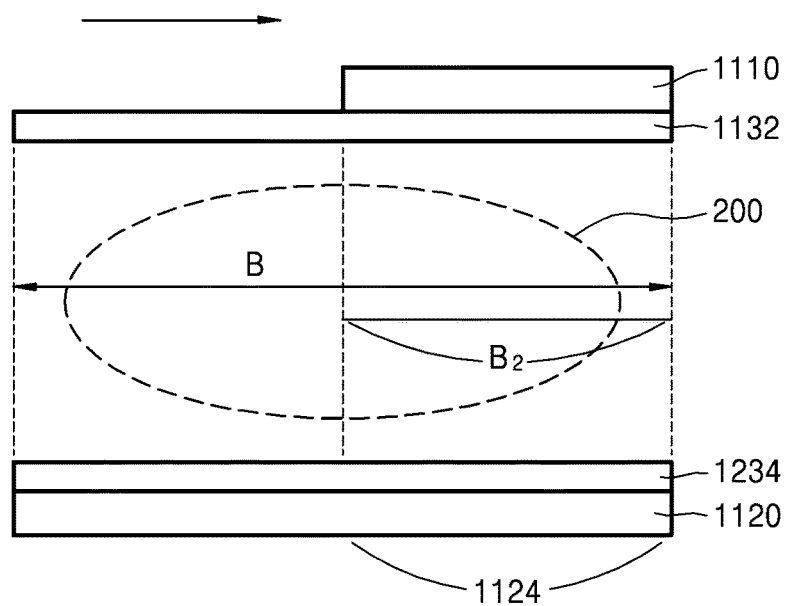

FIGS. 11A and 11B are diagrams for describing an X-ray imaging method when an X-ray generation area A is smaller than a test area B of the object 200 according to an exemplary embodiment. When the X-ray generation area A of an X-ray generator 1110 is smaller than the test area B, the X-ray generator 1110 may move along a first panel 1132 to generate an X-ray, thereby generating the X-ray in the entire test area B of the object 200.

For example, referring to FIG. 11A, the X-ray generator 1110 radiates an X-ray to a first area B1 of the object 200. Then, a first detector 1122 of an X-ray detector 1120 detects an X-ray that was transmitted to the first area B1. Referring to FIG. 11B, the X-ray generator 1110 horizontally moves along the first panel 1132 and then radiates an X-ray to a second area B2 of the object 200. In this regard, the second area B2 and the first area B1 may be disposed so that they do not overlap with each other. Thus, an X-ray radiation dose of the object 200 may be minimized. A second detector 1124 of the X-ray detector 1120 corresponding to the first area B1 detects an X-ray of the second area B2. Although the X-ray generation area A of the X-ray generator 1110 is ½ the test area B in FIGS. 11A and 11B, an exemplary embodiment is not limited thereto. The X-ray generation area A may be 1/n (where n is a natural number equal to or greater than 2) the test area B.

Figure 12A:
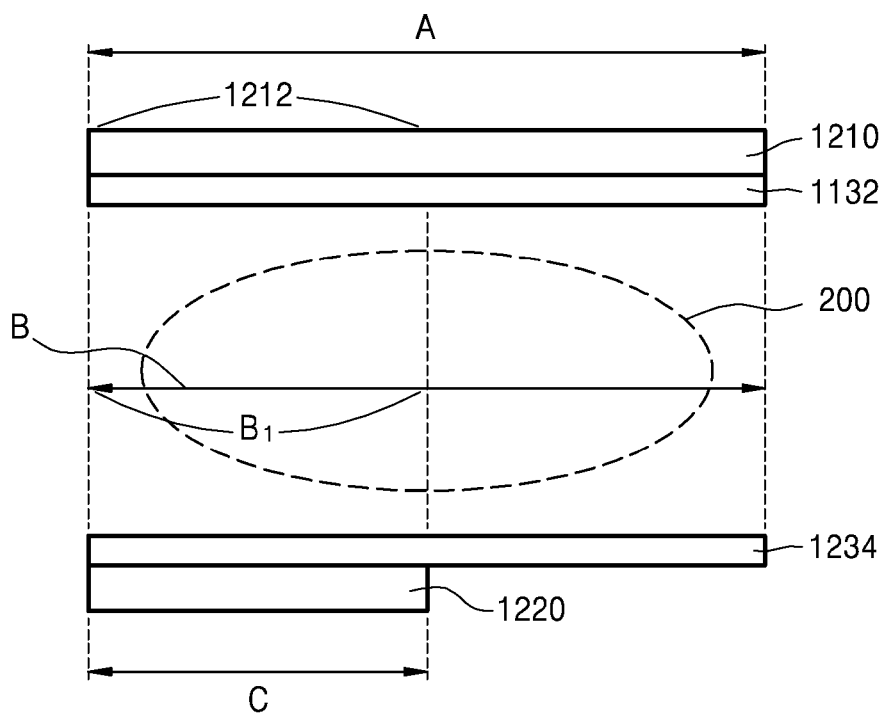
FIGS. 12A and 12B are diagrams for describing an X-ray imaging method according to an exemplary embodiment.
Figure 12B:
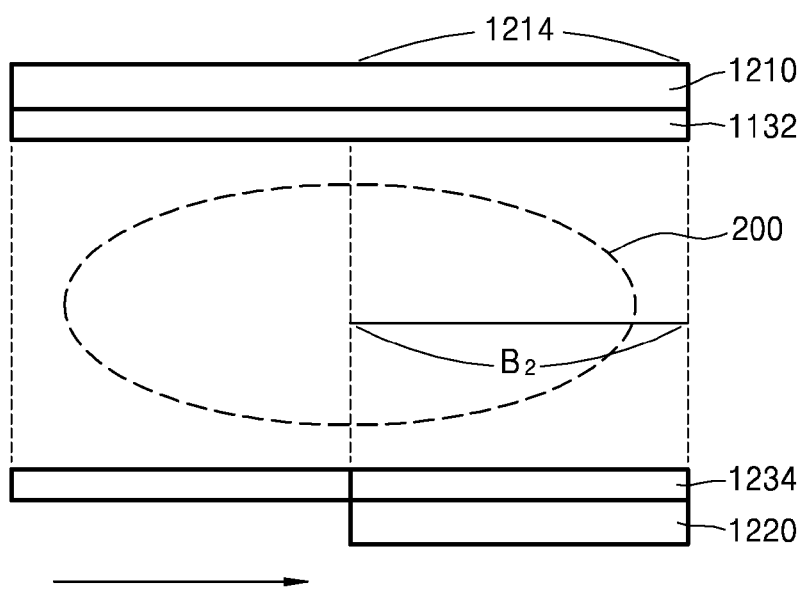

FIGS. 12A and 12B are diagrams for describing an X-ray imaging method when an X-ray detection area C is smaller than the test area B of an object according to an exemplary embodiment. When the X-ray detection area C of the X-ray detector 1120 is smaller than the test area B, the X-ray detector 1120 may move along a second panel 1234 to detect an X-ray, thereby detecting the X-ray that is transmitted to the entire test area B of the object 200.

For example, referring to FIG. 12A, a first X-ray generator 1212 of an X-ray generator 1210 generates X-rays to be transmitted to the first area B1 of the object 200 Then, an X-ray detector 1220 detects an X-ray of the first area B1. Referring to FIG. 12B, the X-ray detector 1220 horizontally moves along the second panel 1234. Then, a second X-ray generator 1214 of the X-ray generator 1210 X-rays to be transmitted to the second area B2 of the object 200. The X-ray detector 1220 detects an X-ray of the second area B2. In this regard, the second area B2 and the first area B1 do not overlap with each other. Thus, an X-ray radiation dose of the object 200 may be minimized. Although the X-ray detection area C of the X-ray detector 1120 is ½ the test area B in FIGS. 12A and 12B, an exemplary embodiment is not limited thereto. The X-ray detection area C may be 1/n (where n is a natural number equal to or greater than 2) the test area B.

In addition, when the X-ray generation area A and the X-ray detection area C are smaller than the test area B and correspond to each other one-to-one, the X-ray generators 1110 and 1210 and the X-ray detectors 1120 and 1220 may be synchronized to image a partial region of the test area B. Each of the X-ray generators 1110 and 1210 and the X-ray detectors 1120 and 1220 may horizontally move along the first and second panels 1132 and 1234 and image other regions of the test area B.

When the X-ray generation area A and the X-ray detection area C are smaller than the test area B, and the X-ray generation area A is smaller than the X-ray detection area C, the X-ray imaging method of FIGS. 12A and 12B may be applied to image a partial region of the test area B. Each of the X-ray generators 1110 and 1210 and the X-ray detectors 1120 and 1220 may horizontally move along the first and second panels 1132 and 1234 and image other regions of the test area B. Furthermore, when the X-ray generation area A and the X-ray detection area C are smaller than the test area B, and the X-ray detection area C is smaller than the X-ray generation area A, the X-ray imaging method of FIGS. 12A and 12B may be applied to image a partial region of the test area B. Each of the X-ray generators 1110 and 1210 and the X-ray detectors 1120 and 1220 may horizontally move along the first and second panels 1132 and 1234 and image other regions of the test area B.

The X-ray imaging apparatus 100 according to an embodiment may acquire a tomography image of the object 200. To acquire the tomography image, the X-ray generators may radiate an X-ray to the object by varying a radiation angle to the object. The X-ray generators according to an embodiment may vary the radiation angle to the object by horizontally moving with respect to the object. In this regard, horizontal moving means horizontal moving of center axes of the X-ray generators.

To acquire the tomography image, the X-ray generators may radiate an X-ray to the object at multiple locations. When the X-ray is radiated at multiple locations, the center axes of the X-ray generators may move in parallel to the object. Furthermore, the X-ray generators may radiate an X-ray by varying a radiation angle according to locations thereof. For example, the X-ray generators may radiate an X-ray to the object vertically at a first location and inclinedly at a second location. In this regard, the X-ray detectors may be disposed under the object. The X-ray detectors may be fixed.

Figure 13A:
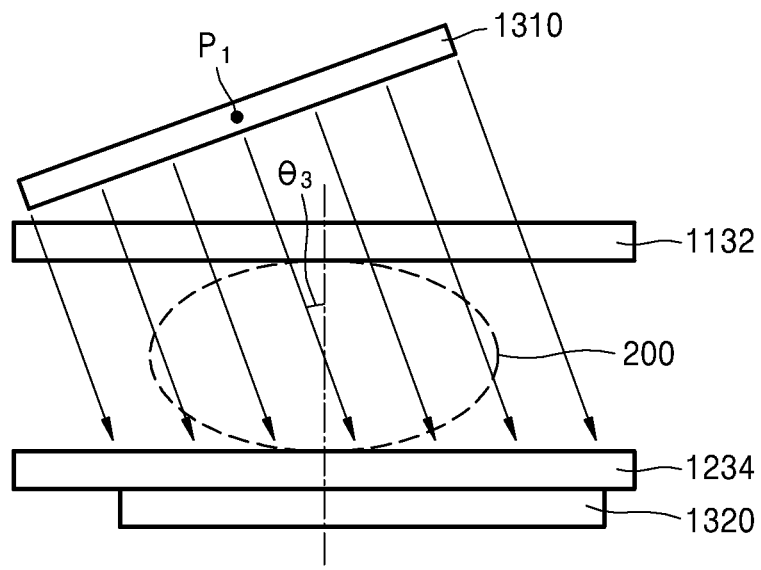
FIGS. 13A, 13B, and 13C are diagrams for describing an X-ray imaging method to acquire a tomography image according to an exemplary embodiment.
Figure 13B:
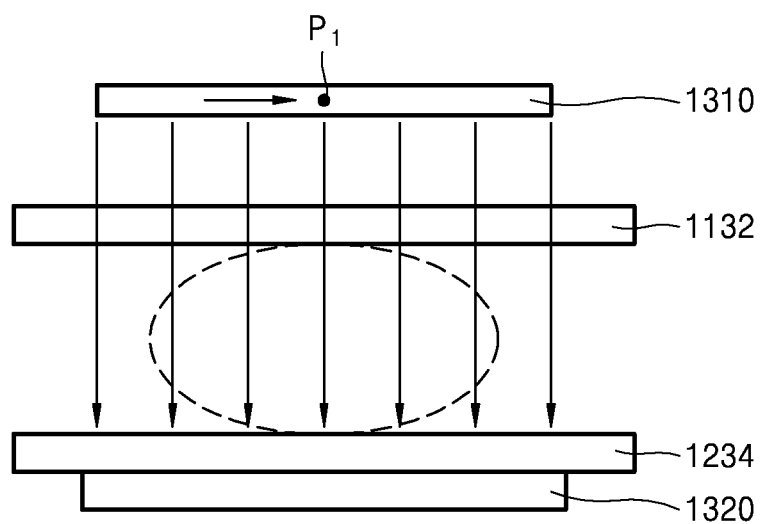
Figure 13C:
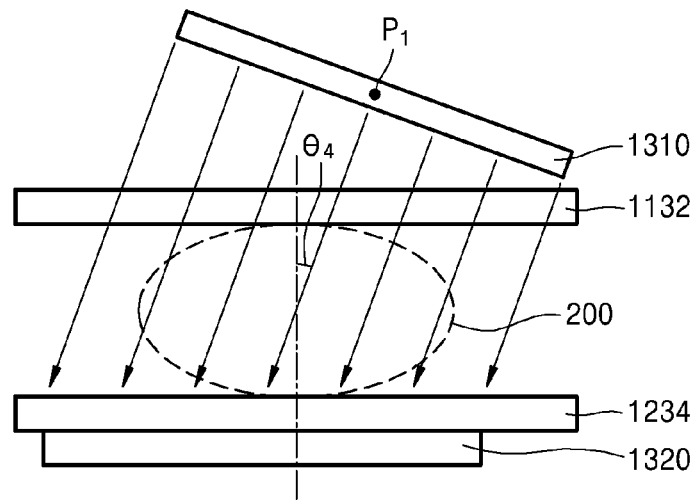

FIGS. 13A through 13C are diagrams for describing an X-ray imaging method to acquire a tomography image according to an exemplary embodiment. Referring to FIG. 13A, when an X-ray generator 1310 is disposed on a left upper portion of the object 200, the X-ray generator 1310 may rotate with respect to a center axis P1 thereof such that an X-ray radiation direction is changed from the left upper portion to a right lower portion. The X-ray generator 1310 radiates an X-ray at a first radiation angle θ1 toward the object 200, and thus an X-ray imaging apparatus may image a first image of the object 200.

The X-ray generator 1310 may move to the right. When the X-ray generator 1310 moves, the center axis P1 of the X-ray generator 1310 may move in parallel to the object 200. When the X-ray generator 1310 is disposed on the object 200, the X-ray generator 1310 may adjust its posture to allow an X-ray to face the object 200. For example, the X-ray generator 1310 may rotate in a clockwise direction with respect to the center axis P1 of the X-ray generator 1310, and thus, as shown in FIG. 13B, the X-ray generator 1310 may be disposed in parallel to the object 200. The X-ray generator 1310 may vertically radiate an X-ray to the object 200. The X-ray imaging apparatus may image a second image of the object 200.

The X-ray generator 1310 may move in parallel to the right until the X-ray generator 1310 is disposed on a right upper portion of the object 200. When the X-ray generator 1310 is disposed on the right upper portion of the object 200, the X-ray generator 1310 may adjust its posture to allow an X-ray generated by the X-ray generator 1310 to be inclinedly radiated to the object 200. For example, as shown in FIG. 13C, the X-ray generator 1310 may rotate in a clockwise direction with respect to the center axis P1 of the X-ray generator 1310. The X-ray generator 1310 may radiate an X-ray at a second radiation angle θ2 toward the object 200, and thus the X-ray imaging apparatus may image a third image of the object 200.

When the X-ray generator 1310 moves in a horizontal direction with respect to an X-ray detector 1320, the X-ray generator 1310 rotates with respect to the center axis P1 thereof according to a location. An order of horizontal movement and rotational movement may be switched, and the second image of the object 200 may be imaged in advance and the first image or the third image may be imaged.

Figure 14A:
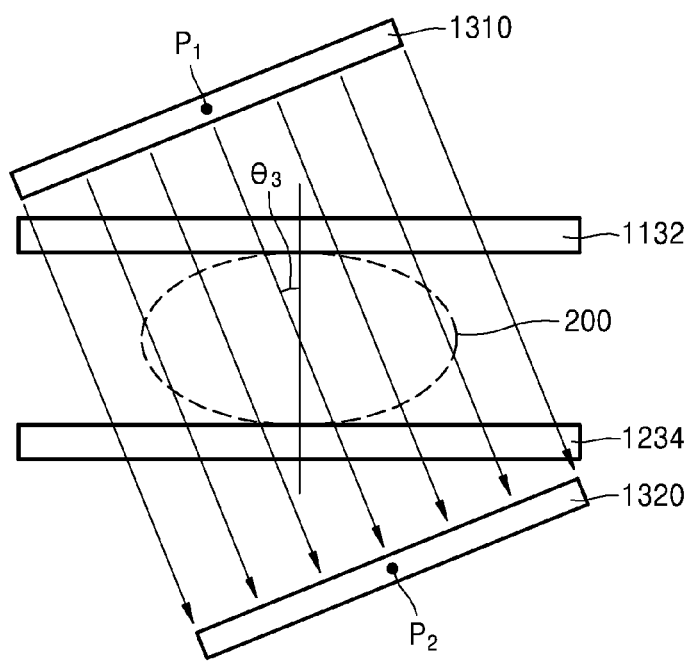
FIGS. 14A, 14B, and 14C are diagrams for describing an X-ray imaging method to acquire a tomography image according to an exemplary embodiment.
Figure 14B:
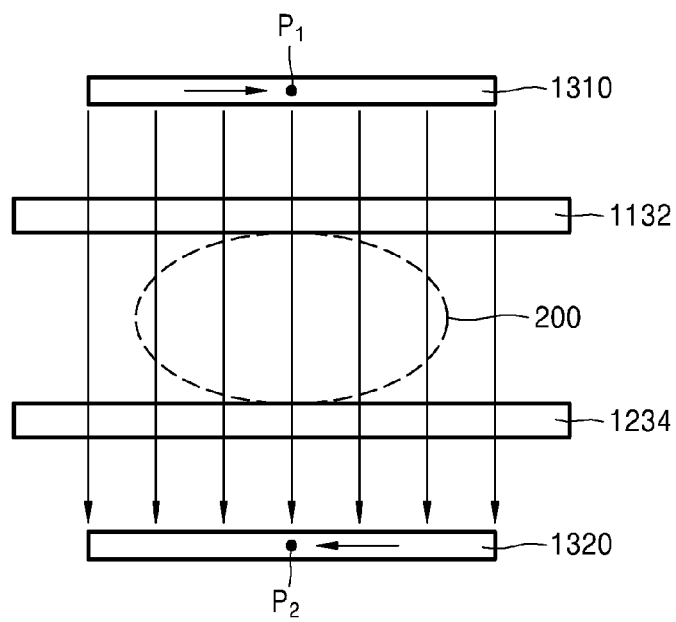
Figure 14C:
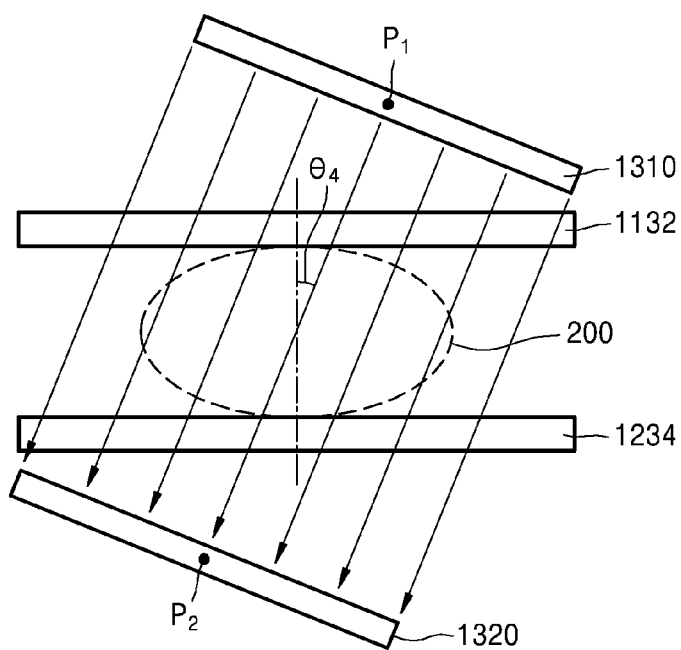

The X-ray detector 1320 may detect an X-ray by moving to correspond to the X-ray generator 1310. FIGS. 14A through 14C are diagrams for describing an X-ray imaging method to acquire a tomography image according to an exemplary embodiment.

Referring to FIG. 14A, when the X-ray generator 1310 is disposed on a left upper portion of the object 200, the X-ray generator 1310 may rotate with respect to the center axis P1 thereof such that an X-ray may be inclinedly radiated to the object 200. In this regard, the X-ray detector 1320 may also move to face the X-ray generator 1310. For example, the X-ray detector 1320 may move to be disposed on a right lower portion of the object 200 and rotate with respect to a center axis P2 of the X-ray detector 1320 such that the X-ray generator 1310 and the X-ray detector 1320 may be disposed in parallel to each other. The X-ray generator 1310 may radiate an X-ray at a first radiation angle θ3 to the object 200, and thus an X-ray imaging apparatus may image a first image of the object 200.

Referring to FIG. 14B, the X-ray generator 1310 may move to be disposed on the object 200. Furthermore, the X-ray generator 1310 may adjust its posture such that the X-ray generator 1310 may be disposed in parallel to the object 200. In this regard, the X-ray detector 1320 may also move. For example, the X-ray detector 1320 may move to be disposed under the object 200 and rotate with respect to the center axis P2 thereof such that the X-ray generator 1310, the object, 200, and the X-ray detector 1320 may be disposed in parallel to each other. The X-ray generator 1310 may vertically radiate an X-ray to the object 200, and thus the X-ray imaging apparatus may acquire a second image of the object 200.

Referring to FIG. 14C, the X-ray generator 1310 may move to a right upper portion of the object 200 and adjust its posture such that an X-ray is inclinedly radiated to the object 200. In this regard, the X-ray detector 1320 may also move to be disposed in parallel to the X-ray generator 1310. For example, the X-ray detector 1320 may move to be disposed on a left lower portion of the object 200 and rotate with respect to the center axis P2 thereof such that the X-ray generator 1310, the object, 200, and the X-ray detector 1320 may be disposed in parallel to each other. The X-ray generator 1310 may radiate an X-ray at a second radiation angle θ4 to the object 200, and thus the X-ray imaging apparatus may acquire a third image of the object 200.

As described above, the X-ray generator 1310 may move to vary a radiation angle of an X-ray and radiate the X-ray to the object 200, thereby simplifying an imaging process for acquiring a tomography image.

Furthermore, the X-ray generator 1310 and the X-ray detector 1320 are fixed whereas the X-ray generator 1310 and the X-ray detector 1320 rotate, and thus imaging may be performed to acquire the tomography image.

Figure 15:
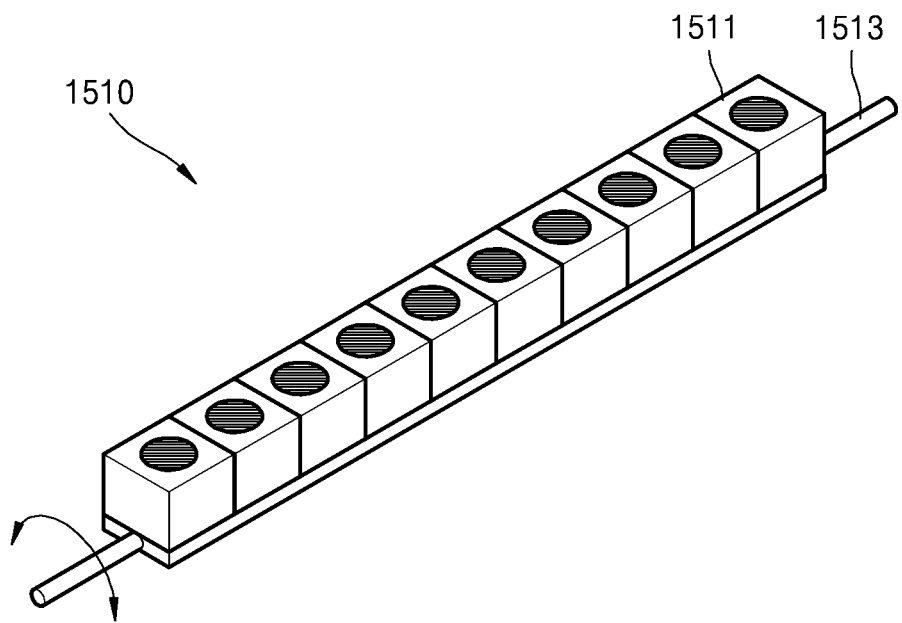
FIG. 15 is a schematic diagram of an X-ray generator according to an exemplary embodiment.

FIG. 15 is a schematic diagram of an X-ray generator 1510 according to an exemplary embodiment. Referring to FIG. 15, the X-ray generator 1510 according to an embodiment may include a plurality of X-ray generation units 1511 arranged in one dimension and a rotation unit 1513 that supports and rotates the X-ray generation units 1511. The X-ray generator 1510 may include a driver (not shown) that drives the rotation unit 1513. If the rotation unit 1513 rotates at a predetermined time interval, the X-ray generation units 1511 disposed on the rotation unit 1513 may radiate an X-ray to an object at different radiation angles at the predetermined time interval. An X-ray detector may include a rotation unit like the X-ray generator 1510.

Figure 16A:
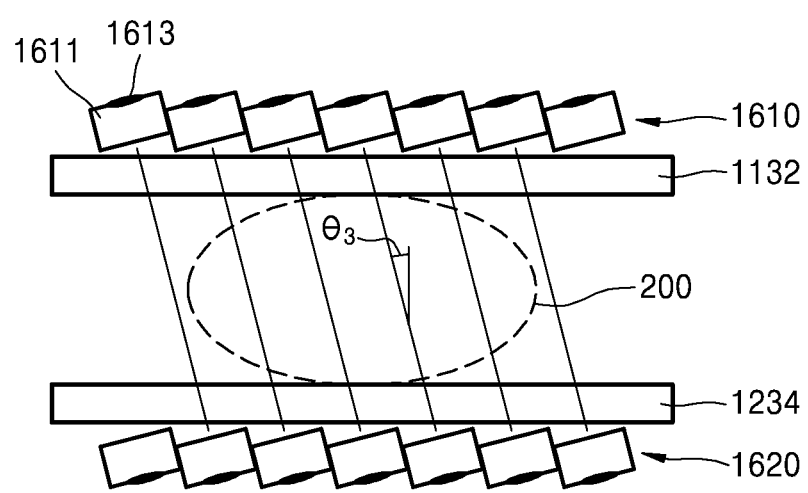
FIGS. 16A, 16B, and 16C are diagrams for describing an X-ray imaging method to acquire a tomography image according to an exemplary embodiment.
Figure 16B:
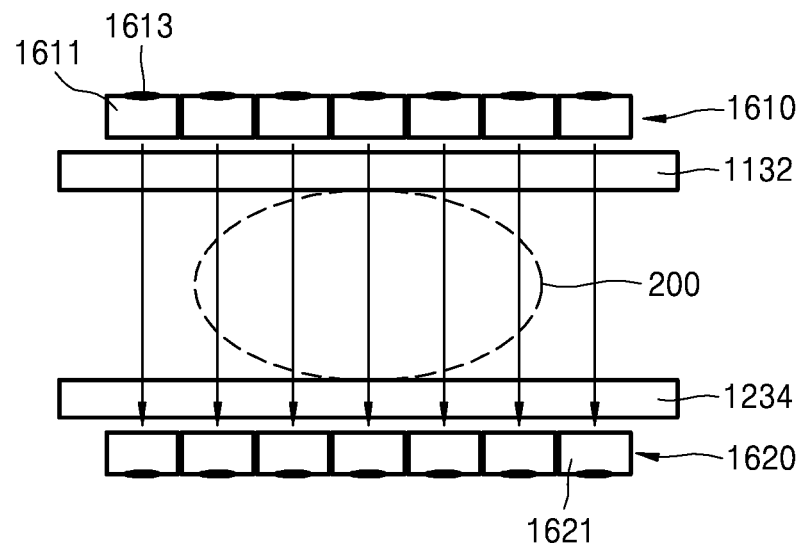
Figure 16C:
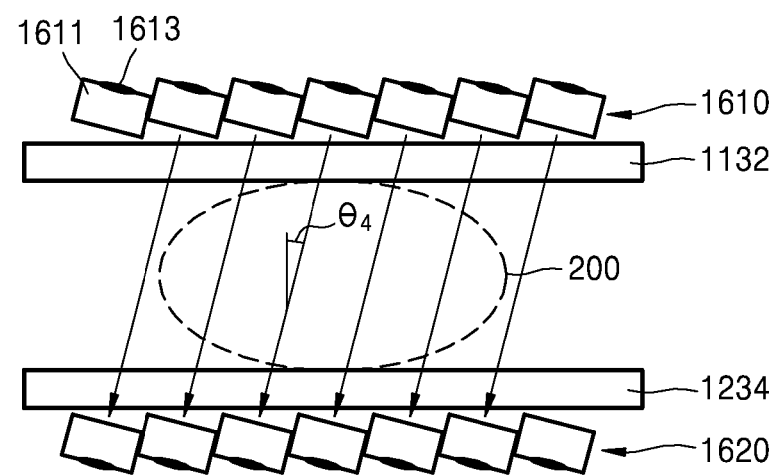

FIGS. 16A through 16C are diagrams for describing an X-ray imaging method to acquire a tomography image according to an exemplary embodiment.

Referring to FIG. 16A, a rotation unit 1613 may rotate such that each X-ray generation unit 1611 of an X-ray generator 1610 may radiate an X-ray to the object 200 at the first radiation angle θ3 at a first time. For example, the rotation unit 1613 may rotate in a counterclockwise direction at the first time. The X-ray generator 1610 may radiate the X-ray to the object 200 at the first radiation angle θ3, and thus an X-ray imaging apparatus may acquire a first image of the object 200.

Referring to FIG. 16B, each X-ray generation unit 1611 rotates in a counterclockwise direction at a second time after a predetermined time elapses and then the X-ray generator 1610 may vertically radiate an X-ray to the object 200. The X-ray imaging apparatus may acquire a second image of the object 200. Furthermore, referring to FIG. 16C, each of the X-ray generation units 1611 rotates in a clockwise direction at a third time after a predetermined time elapses and then the X-ray generator 1610 may vertically radiate an X-ray to the object 200 at the second radiation angle θ4. The X-ray imaging apparatus may acquire a third image of the object 200. In this regard, X-ray detection units 1621 may rotate like the X-ray generation units 1611 to detect an X-ray.

As described above, an X-ray radiation angle may be changed by rotating only the X-ray generation units 1611, thereby simplifying an imaging process for acquiring the tomography image.

Figure 17:
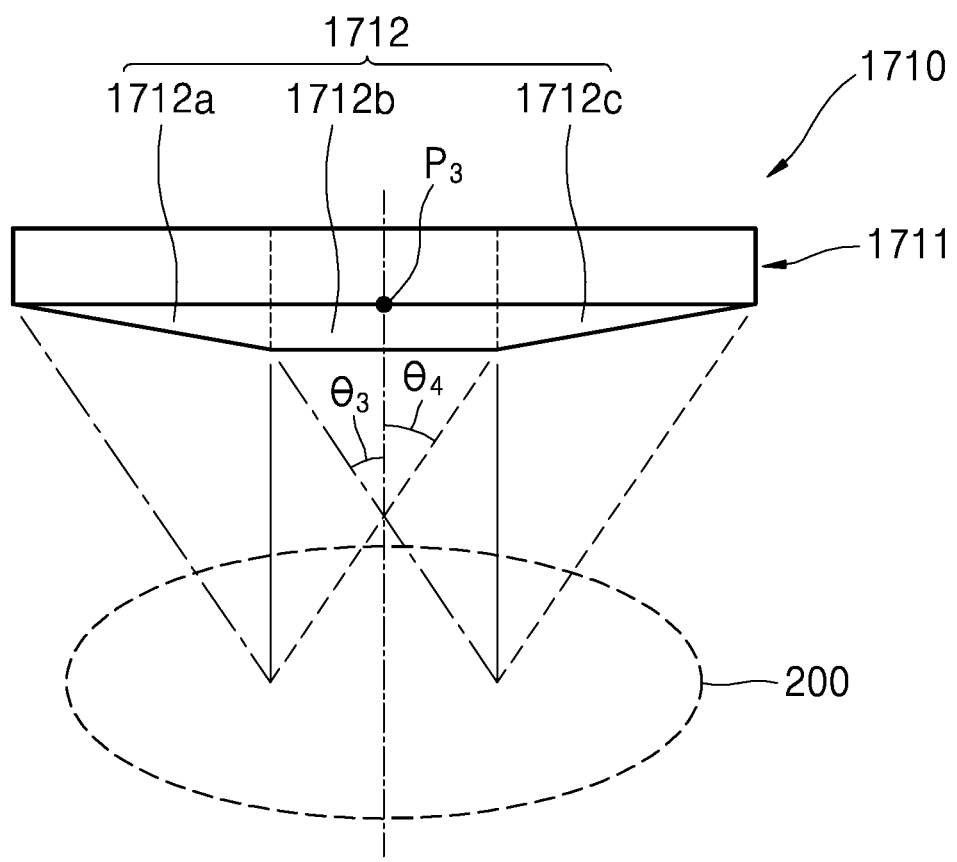
FIG. 17 is a schematic diagram of an X-ray generator used to acquire a tomography image according to an exemplary embodiment.

Furthermore, a shape of an anode electrode among the X-ray generation units 1611 may be used to change the X-ray radiation angle with respect to the object 200. FIG. 17 is a schematic diagram of an X-ray generator 1710 used to acquire a tomography image according to an exemplary embodiment. Referring to FIG. 17, the X-ray generator 1710 may include an anode electrode 1712 that emits an X-ray due to collisions between a plurality of electron emission devices 1711 that are independently driven and electrons. The anode electrode 1712 may have a different thickness with respect to a center axis P3 of the X-ray generator 1710. For example, if the anode electrode 1712 is divided into three regions, a thickness of the first region 1712a increases as the first region 1217a is closer to the center axis P3 of the X-ray generator 1710, a thickness of a second region 1712b is uniform, and a thickness of a third region 1712c decreases as the third region 1712c is farther away from the center axis P3 of the X-ray generator 1710. Thus, an X-ray from the first region 1712a is radiated to the object 200 at the first radiation angle θ3, an X-ray from the second region 1712b may be vertically radiated to the object 200, and an X-ray from the third region 1712c may be radiated to the object 200 at the second radiation angle θ4.

If the electron emission device 1711 corresponding to the first region 1712a emits electrons at a first time, the X-ray generated in the first region 1712a may be radiated to the object 200 at the first radiation angle θ3. If the electron emission device 1711 corresponding to the second region 1712b emits electrons at a second time, the X-ray generated in the second region 1712b may be vertically radiated to the object 200. If the electron emission device 1711 corresponding to the third region 1712c emits electrons at a third time, the X-ray may be generated in the third region 1712c. The X-ray generated in the third region 1712c may be radiated to the object 200 at the second radiation angle θ4. Thus, an X-ray imaging apparatus may perform X-ray imaging to acquire the tomography image by using a shape of the anode electrode 1712.

The X-ray imaging to acquire the tomography image is performed three times. However, this is for convenience of description, and X-ray imaging may be performed two or more times to acquire the tomography image.

The X-ray imaging apparatus according to the present embodiment may further include a sensor that senses the object 200. The sensor may include a plurality of sensors. Each sensor may sense an existence of the object 200 and determine a location of the object 200 based on results of sensing by all the sensors. The sensors may be light sensors (in particular, illumination sensors), touch sensors, etc. In particular, when the sensors are touch sensors, the sensors may be formed as a single pad, i.e., a touch pad.

Figure 18A:
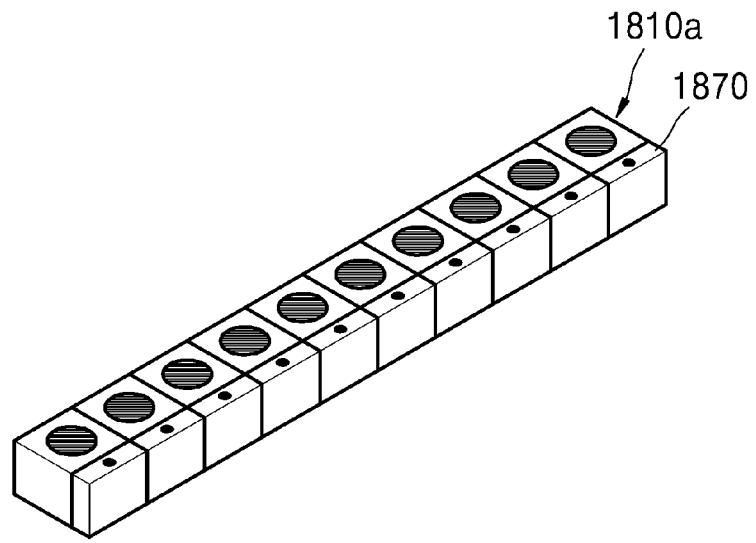
FIGS. 18A and 18B are schematic diagrams of X-ray generators according to an exemplary embodiment.
Figure 18B:
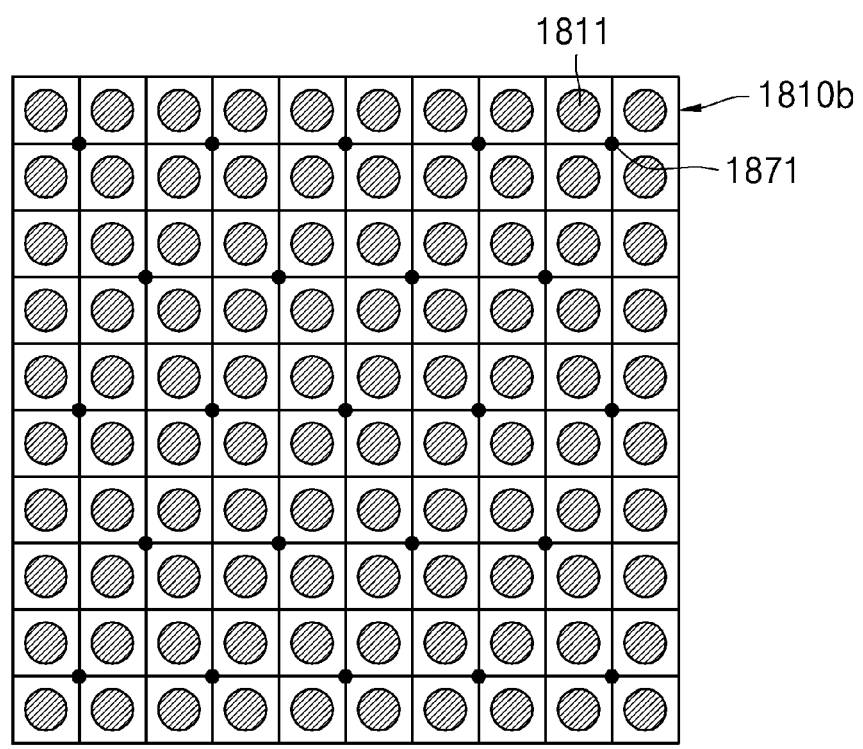

FIGS. 18A and 18B are schematic diagrams of X-ray generators 1810a and 1810b including a plurality of sensors 1871 according to an exemplary embodiment. The sensors 1871 may be arranged to be integrated with the X-ray generators 1810a and 1810b. Referring to FIG. 18A, a 1D sensor array 1870 is disposed at a side of the 1D X-ray generator 1810a so that the 1D X-ray generator 1810a and the 1D sensor array 1870 may be integrated. Alternatively, referring to FIG. 18B, the sensor 1871 may be disposed to be spaced apart from each other on a second dimensional X-ray generator 1810b. The sensors 1871 may be disposed not to overlap with X-ray generation units 1811. In FIG. 18B, the sensors 1871 are disposed on regions in which four X-ray generation units 1811 are adjacent. In particular, the sensors 1871 may be disposed on the same plane of the X-ray generators 1810a and 1810b as an anode electrode (not shown). Thus, an X-ray traveling path is not influenced by the sensors 1871. However, an exemplary embodiment is not limited thereto. Locations of the sensors 1871 may be determined as long as the X-ray traveling path and the sensors 1871 do not overlap with each other.

Although the sensors 1871 are disposed on the entire regions in which the X-ray generators 1810a and 1810b are disposed, an exemplary embodiment is not limited thereto. When a size and location of an object are generally expected, the sensors 1871 are not disposed in a region in which the object is necessarily disposed or in a region in which there is no possibility that the object is to be disposed. The sensors 1871 may be focused in a region corresponding to a boundary of the object. The sensors 1871 disposed on the X-ray generators 1810a and 1810b may be light sensors.

Although the sensors 1871 are integrally formed with the X-ray generators 1810a and 1810b in FIGS. 18A and 18B, an exemplary embodiment is not limited thereto. The sensors 1871 may be integrally formed with X-ray detectors. For example, when X-ray detectors are one dimensional X-ray detectors, the sensors 1871 may be disposed to contact the X-ray detectors. When the X-ray detectors are second dimensional X-ray detectors, the sensors 1871 may be disposed between the X-ray detectors.

Figure 19A:
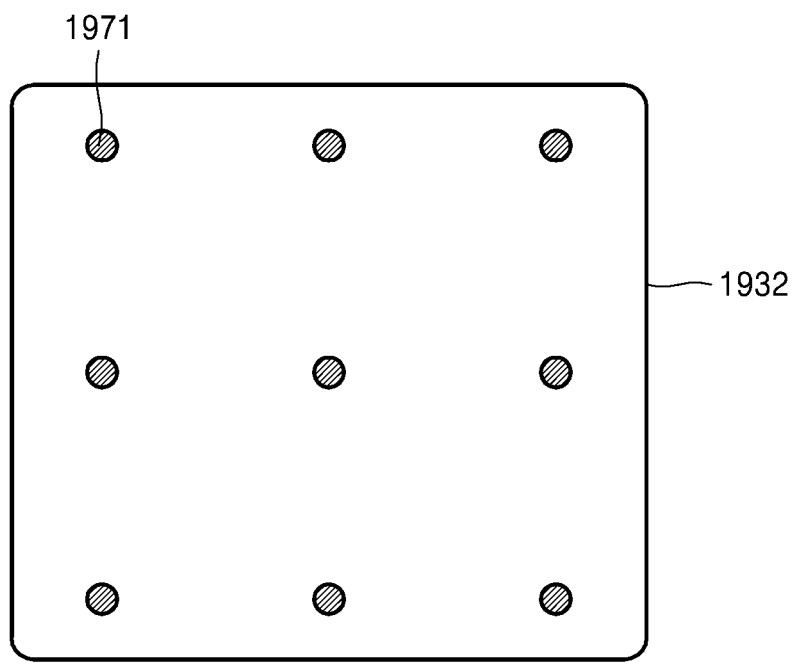
FIGS. 19A and 19B illustrate a panel on which sensors are disposed according to an exemplary embodiment.
Figure 19B:
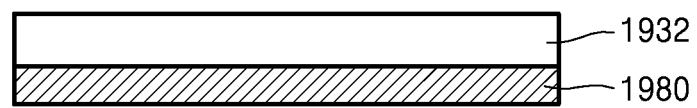

FIGS. 19A and 19B illustrate a panel 1932 on which sensors 1971 are disposed according to an exemplary embodiment. Referring to FIG. 19A, the sensors 1971 may be disposed on the panel 1932. If the sensors 1971 are disposed on an X-ray generator, when the X-ray generator does not cover an object, the X-ray generator needs to be moved in a horizontal direction to detect a location of the object. However, since the panel 1932 covers the object, when the sensors 1971 are disposed on the panel 1932, the object may be more easily detected. The sensors 1971 may be disposed on a surface of the panel 1932 facing the X-ray generator or on a surface of the panel 1932 facing the object. The sensors 1971 disposed on the panel 1932 may be light sensors, touch sensors, etc. When the sensors 1971 are disposed on the panel 1932, the sensors 1971 may be formed of a transparent material to minimize diffusion of an X-ray or absorption by the sensors 1971. In particular, when the sensors 1971 are touch sensors, the sensors 1971 may be implemented as a touch pad 1980.

Figure 20:
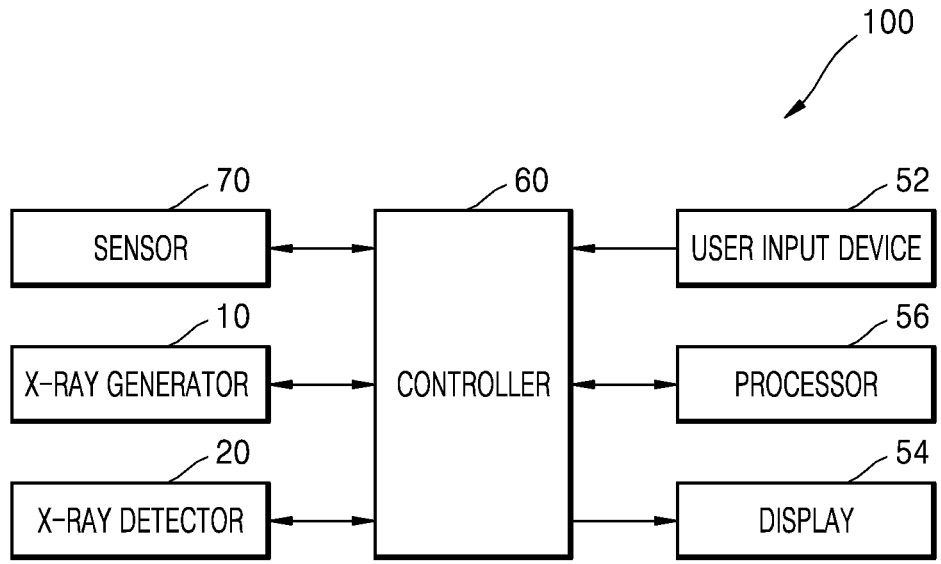
FIG. 20 is a block diagram of an X-ray imaging apparatus according to an exemplary embodiment.

FIG. 20 is a block diagram of the X-ray imaging apparatus 100 of FIG. 1 according to an exemplary embodiment. Referring to FIG. 20, the X-ray imaging apparatus 100 may include an X-ray generator 10, an X-ray detector 20, the user input device 52, a display 54, a processor 56, and a controller 60. The X-ray imaging apparatus 100 may further include a sensor 70 that senses an object.

The X-ray generator 10 radiates an appropriate X-ray to the object as described above. The X-ray generator 10 is described above, and thus a description thereof will not be repeated here. The X-ray detector 20 detects the X-ray that transmitted the object. When the X-ray generator 10 radiates the X-ray, the X-ray detector 20 detects the X-ray that transmitted the object, which is described above, and thus a description thereof will not be repeated here.

The user input device 52 receives an input of an X-ray imaging command from a user such as a medical expert. Information regarding a command to change a location of the X-ray generator 10, a parameter adjustment command to vary an X-ray spectrum, a command regarding a main body of the X-ray imaging apparatus 100 or a movement of the X-ray generator 10, and all commands received from the user is transmitted to the controller 60. The controller 60 controls elements included in the X-ray imaging apparatus 100 according to a user command.

The processor 56 receives an electrical signal corresponding to the X-ray detected by the X-ray detector 20. The processor 56 may preprocess the electrical signal to acquire an image. In this regard, preprocessing may include at least one of offset compensation, algebra conversion, X-ray dose compensation, sensitivity compensation, and beam hardening. The image includes a tomography image.

The processor 56 may preprocess the electrical signal corresponding to the detected X-ray to acquire the image. The processor 56 may preprocess an electrical signal corresponding to the detected X-ray to acquire transparent data and reconfigure the acquired transparent data for each radiation angle to acquire the tomography image.

A location and a type of the sensor 70 are described above, and thus a detailed description thereof will not be repeated here. Each sensor included in the sensor 70 may sense an existence of the object and apply a result of the sensing to the controller 60. Thus, the controller 60 may determine a location of the object by using results of the sensing by the sensors. The controller 60 may control the X-ray generator 10 to allow an X-ray generation unit of the X-ray generator 10 corresponding to the location of the object to generate an X-ray. Furthermore, the controller 60 may control the X-ray detector 20 to allow an X-ray detection unit of the X-ray detector 20 corresponding to the location of the object to detect an X-ray that is transmitted to the object.

Only some of the X-ray generation units operate to image the object, thereby reducing an X-ray radiation dose. Furthermore, only some of the X-ray detection units operate, and thus a lifetime of the X-ray detector 20 may be increased, thereby simplifying signal processing.

Figure 21:
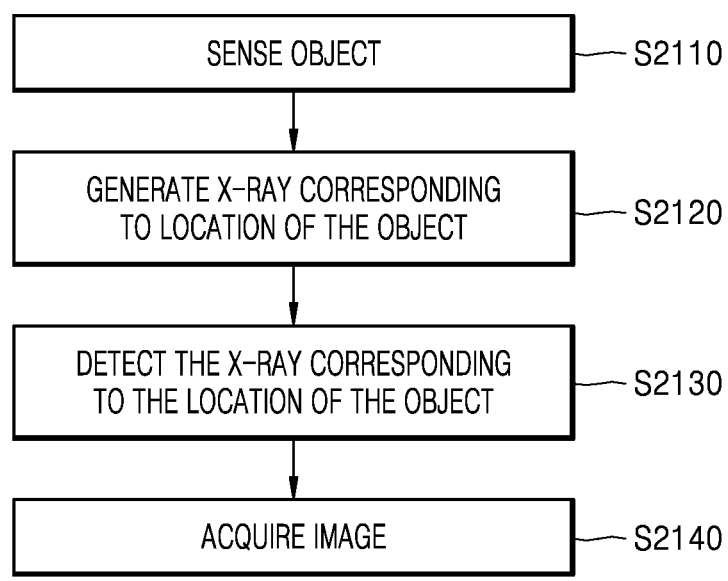
FIG. 21 is a flowchart of an X-ray imaging method according to an exemplary embodiment.

An X-ray imaging method using the sensor 70 will now be described. FIG. 21 is a flowchart of an X-ray imaging method according to an exemplary embodiment. Referring to FIG. 21, the sensor 70 senses the object 200 (operation S2110). If the object 200 is disposed between the first panel 32 and the second panel 34 of the X-ray imaging apparatus 100 of FIG. 1, the X-ray imaging apparatus 100 may move at least one of the first panel 32 and the second panel 34 according to a user command to compress the object 200. If the object 200 contacts the first panel 32 and the second panel 34 or is pressed by the first panel 32 and the second panel 34, each sensor included in the sensor 70 may sense an existence of the object 200. For example, when sensors are illumination sensors, the sensors may sense whether the object 200 exists based on an illumination change, and when the sensors are touch sensors, the sensors may sense whether the object 200 exists according to whether the touch sensors are touched. A result of the sensing by each sensor is applied to the controller 60.

The controller 60 may control the X-ray generator 10 to allow an X-ray generation unit of the X-ray generator 10 corresponding to a location of the object 200 to generate an X-ray by using results of the sensing by the sensor 70

(operation S2120). The controller 60 may determine the location of the object 200 from the result of the sensing by each sensor. For example, the location of the object 200 may be determined from locations of the sensors that detect the illumination change and whether the sensors are touched. The location of the object 200 may be determined to be slightly greater than locations of the sensors. The controller 60 may control the X-ray generation unit of the X-ray generator 10 corresponding to the location of the object 200 to generate the X-ray. An X-ray generation method may vary according to sizes of an X-ray test area and an X-ray generation area, and according to whether an image that is to be imaged is a simple image or a tomography image. This is described above, and thus a detailed description thereof will not be repeated here.

The controller 60 may control the X-ray detector 20 to allow an X-ray detection unit of the X-ray detector 20 corresponding to the location of the object to detect the X-ray (operation S2130). An X-ray detection method may vary according to sizes of the X-ray test area and the X-ray generation area, and according to whether the image that is to be imaged is the simple image or the tomography image. This is described above, and thus a detailed description thereof will not be repeated here. If only the X-ray detection unit of the X-ray detector 20 corresponding to the location of the object detects the X-ray, the X-ray diffused by being transmitted to the object 200 is detected, thereby blocking noise.

Then, the processor 56 may receive an electrical signal corresponding to the X-ray detected by the X-ray detection unit to acquire an image (operation S2140). The acquired image may be displayed on the display 54.

Although the sensor 70 senses the object 200, and the X-ray imaging apparatus 100 operates according to a result of the sensing, an exemplary embodiment is not limited thereto. When the sensor 70 is not included in the X-ray imaging apparatus 100, the X-ray imaging apparatus 100 may perform imaging as described with reference to FIGS. 11A through 16C.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art. For example, each single component may be separated into multiple components which are then separately implemented. Also, separated components may be combined together and implemented as a single component.

What is claimed is:

1. An X-ray generator comprising:
    electron emission devices that are arranged in one dimension or in two dimensions and are configured to emit electrons; and
    an anode electrode configured to emit X-rays by using the electrons emitted by the electron emission devices and comprising regions having irregular thicknesses such that the X-rays emitted from an emission surface of the regions having irregular thicknesses are focused or dispersed,
    wherein the anode electrode comprises:
    first and second layers formed of different materials and disposed in parallel to the electron emission devices;
    wherein a wavelength of the X-rays emitted from the first layer and a wavelength of the X-rays emitted from the second layer are different from each other.

2. The X-ray generator of claim 1, wherein the regions with the irregular thicknesses are disposed so that the anode electrode is configured to be symmetrical with respect to a center axis of the X-ray generator.

3. The X-ray generator of claim 1, wherein a thickness of the anode electrode increases in a direction of edge portions of the anode electrode disposed further away from a center axis of the X-ray generator.

4. The X-ray generator of claim 1, wherein a thickness of the anode electrode decreases in a direction of edge portions of the anode electrode disposed further away from a center axis of the X-ray generator.

5. The X-ray generator of claim 1, wherein at least one among a surface of the anode electrode, on which the electrons are incident, and the emission surface is a curved surface.

6. The X-ray generator of claim 1, wherein at least one among a surface of the anode electrode, on which the electrons are incident, and the emission surface is at least one among a concave surface and a convex surface.

7. The X-ray generator of claim 1, wherein when at least one of the electrons is incident on the first layer, none of the electrons are incident on the second layer.

8. The X-ray generator of claim 1, at least one of the electron emission devices comprises:
    a cathode electrode;
    a gate electrode spaced apart from the cathode electrode; and
    electron emission sources that are disposed on the cathode electrode and are configured to emit the electrons due to a voltage difference between the cathode electrode and the gate electrode.

9. The X-ray generator of claim 8, wherein the cathode electrode included in the electron emission devices is formed on the same substrate.

10. The X-ray generator of claim 8, wherein the gate electrode comprises a mesh structure.

11. The X-ray generator of claim 8, further comprising:
    gate insulation layers disposed between the cathode electrode and the gate electrode.

12. The X-ray generator of claim 11, wherein the gate insulation layers and the electron emission sources are alternately disposed, with respect to one another.

13. An X-ray generator comprising:
    an electron emission device configured to emit electrons; and
    an anode electrode configured to emit X-rays by using the electrons emitted by the electron emission device and comprising regions having irregular thicknesses such that the X-rays emitted from an emission surface of the regions having irregular thicknesses are focused or dispersed,
    wherein the anode electrode comprises: first and second layers formed of different materials and disposed in parallel to the electron emission devices;
    wherein a wavelength of the X-rays emitted from the first layer and a wavelength of the X-rays emitted from the second layer are different from each other.

14. The X-ray generator of claim 13, wherein the regions with the irregular thicknesses are disposed so that the anode electrode is configured to be symmetrical with respect to a center axis of the X-ray generator.

15. The X-ray generator of claim 13, wherein at least one among a surface of the anode electrode, on which the electrons are incident, and the emission surface is at least one among a concave surface and a convex surface.

16. An X-ray imaging apparatus comprising:
the X-ray generator of claim 1; and
an X-ray detector configured to detect the X-ray having passed through an object.

* * * * *